US012419631B2

(12) United States Patent
Rao et al.

(10) Patent No.: US 12,419,631 B2
(45) Date of Patent: Sep. 23, 2025

(54) CONTROLLED SUTURE TENSIONING

(71) Applicant: Edwards Lifesciences Corporation, Irvine, CA (US)

(72) Inventors: Jyoti B. Rao, Brea, CA (US); John Richard Carpenter, Santa Ana, CA (US); Bryan A. Janish, Huntington Beach, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 430 days.

(21) Appl. No.: 18/047,974

(22) Filed: Oct. 19, 2022

(65) Prior Publication Data

US 2023/0069080 A1    Mar. 2, 2023

Related U.S. Application Data

(63) Continuation of application No. PCT/US2021/023392, filed on Mar. 22, 2021.

(60) Provisional application No. 63/014,083, filed on Apr. 22, 2020.

(51) Int. Cl.
*A61B 17/04* (2006.01)

(52) U.S. Cl.
CPC .. *A61B 17/0401* (2013.01); *A61B 2017/0409* (2013.01); *A61B 2017/0443* (2013.01); *A61B 2017/0464* (2013.01); *A61B 2017/0496* (2013.01)

(58) Field of Classification Search
CPC ........ A61B 17/0401; A61B 2017/0409; A61B 2017/0443; A61B 2017/0464; A61B 2017/0496; A61B 17/04; A61B 17/0469; A61B 17/0485; A61B 2017/00243; A61B 2017/0406; A61B 2090/064; A61B 2562/0252

See application file for complete search history.

(56) References Cited

U.S. PATENT DOCUMENTS

| 3,131,957 | A | 5/1964 | Musto |
| 3,752,516 | A | 8/1973 | Mumma |
| 4,403,797 | A | 9/1983 | Ragland, Jr. |
| 4,662,376 | A | 5/1987 | Belanger |
| 4,807,625 | A | 2/1989 | Singleton |

(Continued)

FOREIGN PATENT DOCUMENTS

| EP | 0791330 A3 | 11/1997 |
| EP | 3505077 A1 | 7/2019 |

(Continued)

OTHER PUBLICATIONS

Alfieri, O. el al., "The double-orifice technique in mitral valve repair: a +A198:A225simple solution for complex problems," (2001) J. Thorne. Cardiovasc. Surg., 122(4):674-681.

(Continued)

*Primary Examiner* — Mohamed G Gabr
*Assistant Examiner* — Khoa Tan Le
(74) *Attorney, Agent, or Firm* — Chang & Hale LLP

(57) ABSTRACT

A tensioning device includes an elongate plunger, a plunger track housing configured to receive the plunger therein at least in part, an elongate tube configured to be coupled to the plunger track housing, and an actuator configured to cause axial translation of at least a portion of the plunger within the plunger track housing.

18 Claims, 20 Drawing Sheets

(56) References Cited

U.S. PATENT DOCUMENTS

| | | |
|---|---|---|
| 5,144,961 A | 9/1992 | Chen et al. |
| 5,147,316 A | 9/1992 | Castillenti |
| 5,312,423 A | 5/1994 | Rosenbluth et al. |
| 5,391,176 A | 2/1995 | de la Torre |
| 5,405,352 A | 4/1995 | Weston |
| 5,454,821 A | 10/1995 | Harm et al. |
| 5,472,446 A | 12/1995 | de la Torre |
| 5,507,754 A | 4/1996 | Green et al. |
| 5,527,323 A | 6/1996 | Jervis et al. |
| 5,554,184 A | 9/1996 | Machiraju |
| 5,626,614 A | 5/1997 | Hart |
| 5,643,293 A | 7/1997 | Kogasaka et al. |
| 5,681,331 A | 10/1997 | de la Torre et al. |
| 5,716,368 A | 2/1998 | de la Torre et al. |
| 5,727,569 A | 3/1998 | Benetti et al. |
| 5,728,109 A | 3/1998 | Schulze et al. |
| 5,746,752 A | 5/1998 | Burkhart |
| 5,769,862 A | 6/1998 | Kammerer et al. |
| 5,797,928 A | 8/1998 | Kogasaka |
| 5,824,065 A | 10/1998 | Gross |
| 5,931,868 A | 8/1999 | Gross |
| 5,957,936 A | 9/1999 | Yoon et al. |
| 5,971,447 A | 10/1999 | Steck, III |
| 6,010,531 A | 1/2000 | Donlon et al. |
| 6,074,417 A | 6/2000 | Peredo |
| 6,269,819 B1 | 8/2001 | Oz et al. |
| 6,332,893 B1 | 12/2001 | Mortier et al. |
| 6,544,281 B2 * | 4/2003 | ElAttrache ......... A61B 17/0401 606/232 |
| 6,562,051 B1 | 5/2003 | Bolduc et al. |
| 6,626,930 B1 | 9/2003 | Allen et al. |
| 6,629,534 B1 | 10/2003 | St. Goar et al. |
| 6,752,810 B1 | 6/2004 | Gao et al. |
| 6,840,246 B2 | 1/2005 | Downing |
| 6,921,408 B2 | 7/2005 | Sauer |
| 6,940,246 B2 | 9/2005 | Mochizuki et al. |
| 6,978,176 B2 | 12/2005 | Lattouf |
| 6,991,635 B2 | 1/2006 | Takamoto et al. |
| 6,997,950 B2 | 2/2006 | Chawla |
| 7,112,207 B2 | 9/2006 | Allen et al. |
| 7,291,168 B2 | 11/2007 | Macoviak et al. |
| 7,294,148 B2 | 11/2007 | Mccarthy |
| 7,309,086 B2 | 12/2007 | Carrier |
| 7,316,706 B2 | 1/2008 | Bloom et al. |
| 7,373,207 B2 | 5/2008 | Lattouf |
| 7,431,692 B2 | 10/2008 | Zollinger et al. |
| 7,513,908 B2 | 4/2009 | Lattouf |
| 7,534,260 B2 | 5/2009 | Lattouf |
| 7,608,091 B2 | 10/2009 | Goldfarb et al. |
| 7,618,449 B2 | 11/2009 | Tremulis et al. |
| 7,632,308 B2 | 12/2009 | Loulmet |
| 7,635,386 B1 | 12/2009 | Gammie |
| 7,666,196 B1 | 2/2010 | Miles |
| 7,744,609 B2 | 6/2010 | Allen et al. |
| 7,837,727 B2 | 11/2010 | Goetz et al. |
| 7,871,368 B2 | 1/2011 | Zollinger et al. |
| 7,871,433 B2 | 1/2011 | Lattouf |
| 7,959,650 B2 | 6/2011 | Kaiser et al. |
| 8,029,518 B2 | 10/2011 | Goldfarb et al. |
| 8,029,565 B2 | 10/2011 | Lattouf |
| 8,043,368 B2 | 10/2011 | Crabtree |
| 8,147,542 B2 | 4/2012 | Maisano et al. |
| 8,187,323 B2 | 5/2012 | Mortier et al. |
| 8,226,711 B2 | 7/2012 | Mortier et al. |
| 8,241,304 B2 | 8/2012 | Bachman |
| 8,252,050 B2 | 8/2012 | Maisano et al. |
| 8,292,884 B2 | 10/2012 | Levine et al. |
| 8,303,622 B2 | 11/2012 | Alkhatib |
| 8,333,788 B2 | 12/2012 | Maiorino |
| 8,382,829 B1 | 2/2013 | Call et al. |
| 8,439,969 B2 | 5/2013 | Gillinov et al. |
| 8,454,656 B2 | 6/2013 | Tuval |
| 8,465,500 B2 | 6/2013 | Speziali |
| 8,475,525 B2 | 7/2013 | Maisano et al. |
| 8,500,800 B2 | 8/2013 | Maisano et al. |
| 8,608,758 B2 | 12/2013 | Singhatat et al. |
| 8,663,278 B2 | 3/2014 | Mabuchi et al. |
| 8,771,296 B2 | 7/2014 | Nobles et al. |
| 8,828,053 B2 | 9/2014 | Sengun et al. |
| 8,852,213 B2 | 10/2014 | Gammie et al. |
| 8,888,791 B2 | 11/2014 | Jaramillo et al. |
| 8,940,008 B2 | 1/2015 | Kunis |
| 9,131,884 B2 | 9/2015 | Holmes et al. |
| 9,192,287 B2 | 11/2015 | Saadat et al. |
| 2002/0013571 A1 | 1/2002 | Goldfarb et al. |
| 2003/0023254 A1 | 1/2003 | Chiu |
| 2003/0094180 A1 | 5/2003 | Benetti |
| 2003/0105519 A1 | 6/2003 | Fasol et al. |
| 2003/0120264 A1 | 6/2003 | Lattouf |
| 2003/0120341 A1 | 6/2003 | Shennib et al. |
| 2003/0208210 A1 * | 11/2003 | Dreyfuss ............ A61B 17/0483 606/144 |
| 2004/0044365 A1 | 3/2004 | Bachman |
| 2004/0093023 A1 | 5/2004 | Allen et al. |
| 2004/0199183 A1 | 10/2004 | Oz et al. |
| 2005/0004667 A1 | 1/2005 | Swinford et al. |
| 2005/0019735 A1 | 1/2005 | Demas |
| 2005/0075654 A1 | 4/2005 | Kelleher |
| 2005/0119735 A1 | 6/2005 | Spence et al. |
| 2005/0149067 A1 | 7/2005 | Takemoto et al. |
| 2005/0149093 A1 | 7/2005 | Pokorney |
| 2005/0154402 A1 | 7/2005 | Sauer et al. |
| 2005/0216036 A1 | 9/2005 | Nakao |
| 2005/0216077 A1 | 9/2005 | Mathis et al. |
| 2005/0261710 A1 | 11/2005 | Sakamoto et al. |
| 2005/0267493 A1 | 12/2005 | Schreck et al. |
| 2006/0030866 A1 | 2/2006 | Schreck |
| 2006/0100698 A1 | 5/2006 | Lattouf |
| 2006/0111739 A1 | 5/2006 | Staufer et al. |
| 2006/0167541 A1 | 7/2006 | Lattouf |
| 2006/0190030 A1 | 8/2006 | To et al. |
| 2006/0282088 A1 | 12/2006 | Ryan |
| 2007/0001857 A1 | 1/2007 | Hartmann et al. |
| 2007/0049952 A1 | 3/2007 | Weiss |
| 2007/0055292 A1 | 3/2007 | Ortiz et al. |
| 2007/0112422 A1 | 5/2007 | Dehdashtian |
| 2007/0112425 A1 | 5/2007 | Schaller et al. |
| 2007/0118151 A1 | 5/2007 | Davidson |
| 2007/0118154 A1 | 5/2007 | Crabtree |
| 2007/0149995 A1 | 6/2007 | Quinn et al. |
| 2007/0197858 A1 | 8/2007 | Goldfarb et al. |
| 2007/0213582 A1 | 9/2007 | Zollinger et al. |
| 2007/0270793 A1 | 11/2007 | Lattouf |
| 2008/0004597 A1 | 1/2008 | Lattouf et al. |
| 2008/0009888 A1 | 1/2008 | Ewers et al. |
| 2008/0065203 A1 | 3/2008 | Khalapyan |
| 2008/0140093 A1 | 6/2008 | Stone et al. |
| 2008/0167714 A1 | 7/2008 | St. Goar et al. |
| 2008/0188893 A1 | 8/2008 | Selvitelli et al. |
| 2008/0195126 A1 | 8/2008 | Solem |
| 2008/0228223 A1 | 9/2008 | Alkhatib |
| 2008/0249504 A1 | 10/2008 | Lattouf et al. |
| 2008/0269781 A1 | 10/2008 | Funamura et al. |
| 2009/0005863 A1 | 1/2009 | Goetz et al. |
| 2009/0043153 A1 | 2/2009 | Zollinger et al. |
| 2009/0105729 A1 | 4/2009 | Zentgraf |
| 2009/0105751 A1 | 4/2009 | Zentgraf |
| 2009/0276038 A1 | 11/2009 | Tremulis et al. |
| 2010/0023056 A1 | 1/2010 | Johansson et al. |
| 2010/0023117 A1 | 1/2010 | Yoganathan et al. |
| 2010/0023118 A1 | 1/2010 | Medlock et al. |
| 2010/0042147 A1 | 2/2010 | Janovsky et al. |
| 2010/0174297 A1 | 7/2010 | Speziali |
| 2010/0179574 A1 | 7/2010 | Longoria et al. |
| 2010/0210899 A1 | 8/2010 | Schankereli |
| 2010/0298930 A1 | 11/2010 | Orlov |
| 2011/0015476 A1 | 1/2011 | Franco |
| 2011/0022083 A1 | 1/2011 | DiMatteo et al. |
| 2011/0022084 A1 | 1/2011 | Sengun et al. |
| 2011/0028995 A1 | 2/2011 | Miraki et al. |
| 2011/0029071 A1 | 2/2011 | Zlotnick et al. |
| 2011/0060407 A1 | 3/2011 | Ketai et al. |
| 2011/0106106 A1 | 5/2011 | Meier et al. |
| 2011/0144743 A1 | 6/2011 | Lattouf |

(56) References Cited

U.S. PATENT DOCUMENTS

| | | | |
|---|---|---|---|
| 2011/0264208 A1 | 10/2011 | Duffy et al. | |
| 2011/0270278 A1 | 11/2011 | Overes et al. | |
| 2011/0288637 A1 | 11/2011 | De Marchena | |
| 2011/0307055 A1 | 12/2011 | Goldfarb et al. | |
| 2012/0004669 A1 | 1/2012 | Overes et al. | |
| 2012/0143215 A1 | 6/2012 | Corrao et al. | |
| 2012/0150223 A1 | 6/2012 | Manos et al. | |
| 2012/0179184 A1 | 7/2012 | Orlov | |
| 2012/0184971 A1 | 7/2012 | Zentgraf et al. | |
| 2012/0203072 A1 | 8/2012 | Lattouf et al. | |
| 2012/0226294 A1 | 9/2012 | Tuval | |
| 2012/0226349 A1 | 9/2012 | Tuval et al. | |
| 2013/0018459 A1 | 1/2013 | Maisano et al. | |
| 2013/0035757 A1 | 2/2013 | Zentgraf et al. | |
| 2013/0109910 A1* | 5/2013 | Alexander | A61B 17/42 600/204 |
| 2013/0253641 A1 | 9/2013 | Lattouf | |
| 2013/0282059 A1 | 10/2013 | Ketai et al. | |
| 2013/0345749 A1 | 12/2013 | Sullivan et al. | |
| 2014/0031926 A1 | 1/2014 | Kudlik et al. | |
| 2014/0039607 A1 | 2/2014 | Kovach | |
| 2014/0067052 A1 | 3/2014 | Chau et al. | |
| 2014/0114404 A1 | 4/2014 | Gammie et al. | |
| 2014/0214152 A1 | 7/2014 | Bielefeld | |
| 2014/0243968 A1 | 8/2014 | Padala | |
| 2014/0358150 A1* | 12/2014 | Kaufman | A61B 17/7001 606/90 |
| 2014/0364938 A1 | 12/2014 | Longoria et al. | |
| 2015/0032127 A1 | 1/2015 | Gammie et al. | |
| 2015/0045879 A1 | 2/2015 | Longoria et al. | |
| 2016/0367368 A1* | 12/2016 | Vidlund | A61B 90/06 |
| 2019/0175346 A1 | 6/2019 | Schaffner et al. | |
| 2019/0290420 A1* | 9/2019 | Dougherty | A61F 2/0811 |
| 2020/0155315 A1 | 5/2020 | Zhang et al. | |

FOREIGN PATENT DOCUMENTS

| | | |
|---|---|---|
| JP | 2013517110 A | 5/2013 |
| WO | 2004037463 A1 | 5/2004 |
| WO | 2006127509 A2 | 11/2006 |
| WO | 2007100268 A2 | 9/2007 |
| WO | 2007119057 A1 | 10/2007 |
| WO | 2008013869 A2 | 1/2008 |
| WO | 2008124110 A3 | 12/2008 |
| WO | 2008143740 A3 | 2/2009 |
| WO | 2006078694 A3 | 4/2009 |
| WO | 2009081396 A2 | 7/2009 |
| WO | 2010070649 A1 | 6/2010 |
| WO | 2010105046 A1 | 9/2010 |
| WO | 2012137208 A1 | 10/2012 |
| WO | 2013003228 A1 | 1/2013 |
| WO | 2014093861 A1 | 6/2014 |
| WO | 2015020816 A1 | 2/2015 |
| WO | 2016192481 A1 | 12/2016 |

OTHER PUBLICATIONS

Barbero-Marcial, M. et al., "Transxiphoid Approach Without Median Sternotomy for the Repair of Atrial Septa! Defects," (1998) Ann. Thorne. Surg., 65(3):771-774.

Braunberger, E. et al., "Very long-term results (more than 20 years) of valve repair with Carpentier's echniques in nonheumatic mitral valve insufficiency," (2001) Circulation, I 04:1-8-1-11.

Carpentier, Alain, "Cardiac valve surgery—the 'French coffection'," The Journal of Thoracic and Cardiovascular Surgery, vol. 86, No. 3, Sep. 1983, 15 pages.

David, T. E. et al., "Mitral valve repair by replacement of chordae tendineae with polytetrafluoroethylene sutures," (1991) J. Thorne. Cardiovasc. Surg., 101 (3 ):495-50 I.

David, T. E. et al., "Replacement of chordae tendineae with Gore-Tex sutures: a ten-year experience," (1996) J. Heart Valve Dis., 5 ( 4 ):352-355.

Doty, D. B. et al., "Full-Spectrum Cardiac Surgery Through a Minimal Incision: Mini-Sternotomy (Lower Half) Technique," ( 1998) Ann. Thorne. Surg., 65(2):573-577.

Duran, C. M. G. et al., "Techniques for ensuring the correct length of new mitral chords," (2003) .I. Heart Valve Dis., 12(2):156-161.

Eishi, K. et al., "Long-term results of artificial chordae implantation in patients with mitral valve prolapse," (1997) J. Heall Valve Dis., 6(6):594-598.

Frater, R. W. M. ct al., "Chordal replacement in mitral valve repair," ( 1990) Circulation, 82(suppl. IV):IV-125-IV-130.

Frater, R. W. M., "Anatomical rules for the plastic repair of a diseased mitral valve," ( 1964) Thorax. 19:458-464.

Huber, C.H. et al., "Direct Access Valve Replacement (DAVR)—are we entering a new era in cardiac surgery?" (2006) European Journal ofCardio-thoracic Surgery, 29:380-385.

Hvass, U. et al., "Papillary Muscle Sling: A New Functional Approach to Mitra! Repair in Patients With Ischernic Left Ventricular Dysfunction and Functional Mitral Regurgitation," (2003) Ann. Thorne. Surg., 75:809-811.

Kasegawa, H. ct al., "Simple method for detennining proper length of allificial chordae in mitral valve repair," ( 1994) Ann. Thorne. Surg., 57(1 ):237-239.

Kobayashi, J. et al., "Ten-year experience of chordal replacement with expanded polytetrafluoroethylene in mitral valve repair," (2000) Circulation, J 02(19 Suppl 3):1ii-30-Jii-34.

Kunzelman, K. et al., "Replacement of mitral valve posterior chordae tenclincae with expanded polytetrafluorocthylonc suture: a finite element study," (1996) J. Card. Surg., 11(2):136-145.

Langer, F. et al., "RING plus STRING: Papillary muscle repositioning as an adjunctive repair technique for ischemic mitral regurgitation," (2007) J. Thorne. Cardiovasc. Surg., 133( I): 247-249.

Maisano, F. et al., "The double-orifice technique as a standardized approach to treat mitral regurgitation due to severe rnyxomatous disease: surgical technique." (2000) European Journal of Cardio-thorncic Surgery, 17(3):201-205.

Merendino, K. A. et al., "The open con-ection of rheumatic mitral regurgitation and/or stenosis with special reference to regurgitation treated by posteromedial annuloplasty utilizing a pump-oxygenator," (1959) Annals of Surgery, 150(1 ):5-22.

Minatoya, K. et al., "Pathologic aspects of polytetrafluoroethylene sutures in human heart," ( 1996) Ann. Thorac. Surg., 61 (3 ):883-887.

Mohty, D. ct al., "Very long-term survival and durability ofmitral valve repair for mitral valve prolapse," (2001) Circulation, 104:1-1-1-7.

*Neochord, Inc.* v. *University of Maryland, Bal tim ore,* Case No. JPR2016-00208, Decision on Institution of Inter Faries Review,37 CFR §42. I 08, Paper 6, Entered May 24, 2016, 28 pages.

*Neochord, Inc.* v. *University of Maryland, Baltimore,* Case No. IPR2016-00208, Declaration of Dr. Lishan Aklog, dated Nov. 17, 2015, 91 pages.

*Neochord, Inc.* v. *University of Maryland, Baltimore,* Case No. IPR2016-00208, Petition for inter ParlesReview of U.S. Pat. No. 7,635,386, dated Nov. 18, 2015, 65 pages.

Nigro, J. J. et al., "Neochordal repair of the posterior mitral leaflet," (2004) J. Thorne. Cardiovasc. Surg., 127(2):440-447.

Phillips, M. R. et al., "Repair of anterior leaflet mitral valve prolapse: chordal replacement versus chordal shrntening," (2000) Ann. Thorac. Surg., 69(1 ):25-29.

Russo, M. J. ct al. • Transapical Approach for Mitral Valve Repair during Insertion of a Left Ventricular Assist Device, Hindawi Publishing Corporation, The Scientific World Journal, vol. 2013, Article ID 925310, [ online], Retrieved from the internet: <URL: http://dx.doi.org/J 0.1155/2013/92531 O> Apr. 11, 2013, 4 pages.

Sarsam, M.A. I., "Simplified technique for determining the length of artificial cl1ordae in mitral valve repair," (2002) Ann. Thorac. Surg., 73(5): 1659-1660.

Savage, E. B. et al., Use of mitral valve repair: analysis of contemporary United States experience reported to the society of thoracic surgeons national cardiac database, . . . (2003) Ann. Thorne. Surg., 75:820-825.

(56) References Cited

OTHER PUBLICATIONS

Speziali, G. et al., "Coll'ection of Mitral Valve Regurgitation by Off-Pump, Transapical Placement of Artificial Chordae Tendinae, Results of the European TACT Trial," AATS 93rd Annual Meeting 2013, www.aats.org, 26 pages.

Suematsu, Y. et al., "Three-dimensional echo-guided beating heaii surgery without cardiopulmonary bypass: Atrial septa! defect closure in a swine model," (2005) J. Thorne. Cardiovasc. Surg., 130: 1348-1357.

Von Oppell, U. O. et al., "Chordal replacement for both minimally invasive and conventional mitral valve surgery using promcasurcd Gore-Tex loops," (2000) Ann. Thorne. Surg., 70(6):2166-2168.

Zussa, C. et al., Artificial mitral valve chordae: experimental and clinical experience;• ( 1990) Ann. Thorne. Surg., 50(3):367-373.

Zussa, C. et al., "Seven-year experience with chordal replacement with expanded polytetrafluoroethylene in floppyrnitral valve," (1994)1. Thorac. Cardiovasc. Surg., 108(1):37-41.

Zussa, C. et al., "Surgical technique for artificial mitral chordae implantation," ( 1991) Journal of Cardiac Surgery, 6(4):432-438.

Zussa, C., "Artificial chordae," (1995) J. Heart Valve Dis., 4(2):S249-S256.

\* cited by examiner

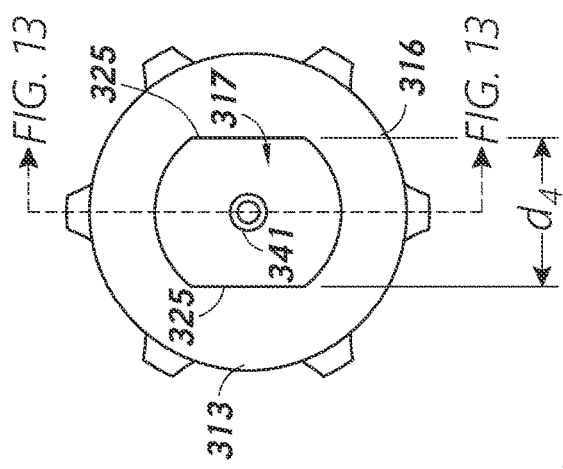
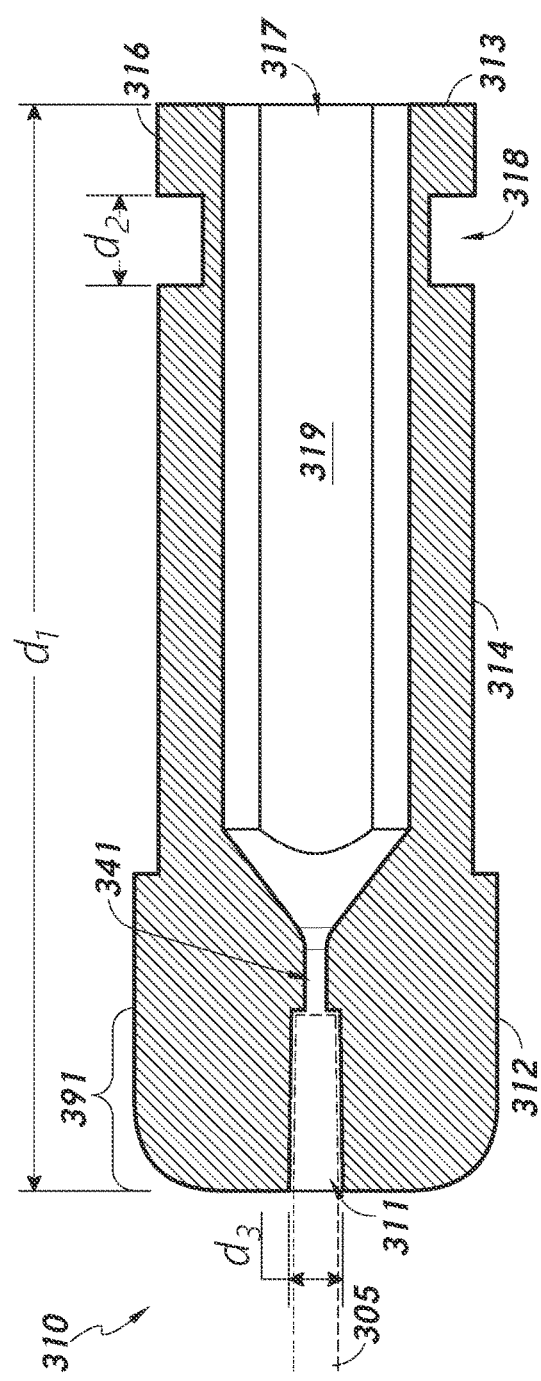
FIG. 13
FIG. 14

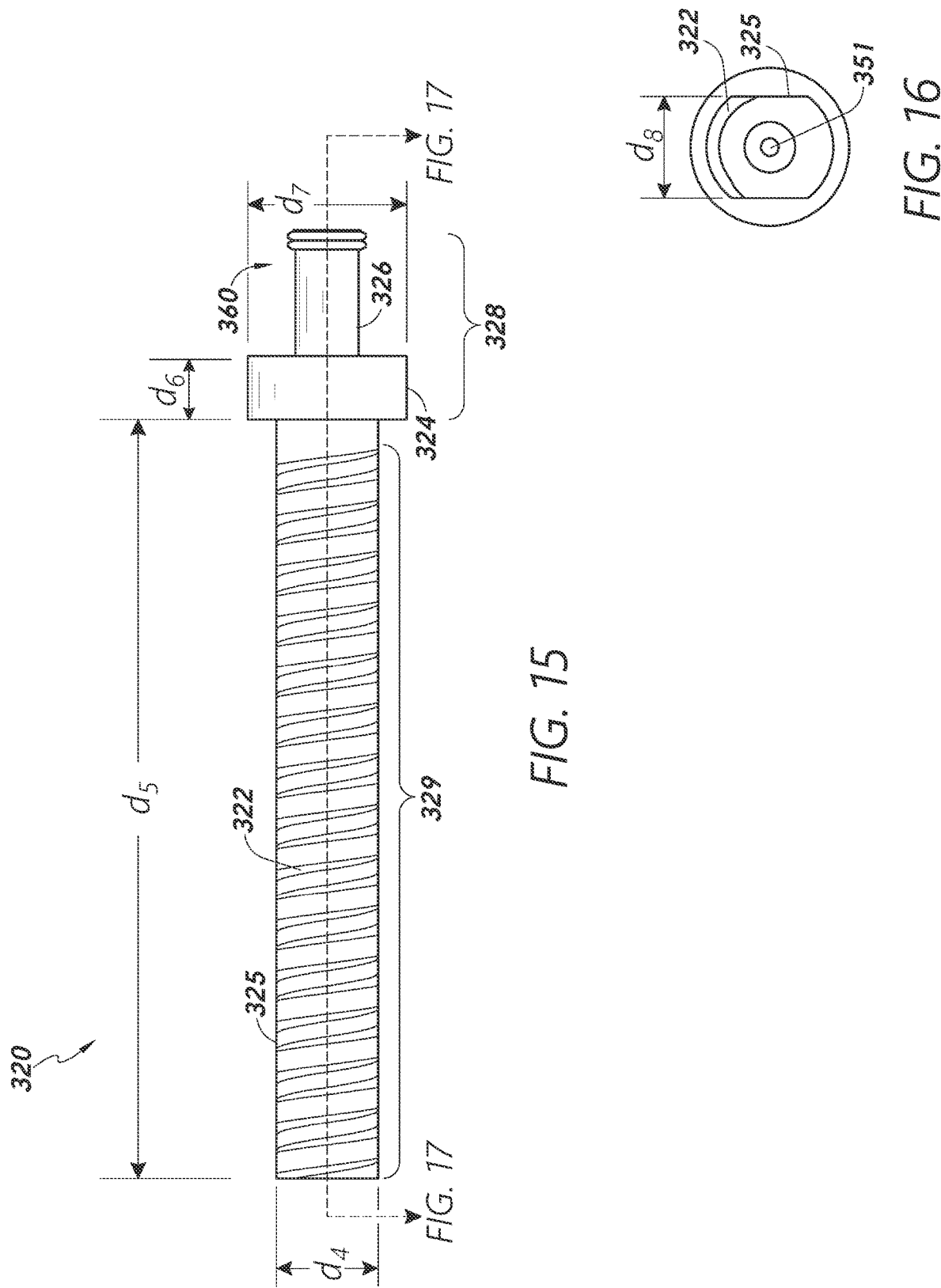

CONTROLLED SUTURE TENSIONING

CROSS REFERENCE TO RELATED APPLICATIONS

This application is a continuation of International Patent Application No. PCT/US2021/023392, filed Mar. 22, 2021, which claims the benefit of U.S. Patent Application No. 63/014,083, filed on Apr. 22, 2020, the entire disclosures all of which are hereby incorporated by reference for all purposes.

BACKGROUND

Technical Field

The present disclosure generally relates to the field of suture tensioning.

Description of Related Art

Certain medical and other procedures involve the use of sutures or other similar devices. The tension of such suture(s) can affect the behavior and/or efficacy of the sutures over time.

SUMMARY

Described herein are methods and devices that facilitate the tensioning of sutures, such as sutures used in connection with cardiac leaflet tissue anchors and/or other heart valve repair solutions.

In some implementations, the present disclosure relates to a tensioning device comprising an elongate plunger, a plunger track housing configured to receive the plunger therein at least in part, an elongate tube configured to be coupled to the plunger track housing, and an actuator configured to cause axial translation of at least a portion of the plunger within the plunger track housing.

The plunger can have a suture-fixation feature associated therewith. For example, the suture-fixation feature may include a Luer assembly. In some examples, the suture-fixation feature includes a radially-projecting form configured to have suture wound thereabout. In some examples, the plunger includes radially-projecting screw threads and the actuator includes screw threads configured to mate with the screw threads of the plunger. For example, the screw threads of the plunger can be radially flattened over at least one circumferential segment of the plunger and the plunger track can include an axial opening having a truncated circle shape and configured to fit the plunger therein.

In some examples, the plunger track housing includes a tube-fit channel open on a distal end of the plunger track housing and configured to receive a proximal end of the tube. The actuator can be configured to be rotatably secured to a proximal end of the plunger track housing. For example, the plunger track housing can include a radially-open circumferential channel on a proximal side of the plunger track housing. In some examples, the actuator includes one or more radially-oriented threaded apertures configured to have one or more respective setscrews disposed therein and the apertures are configured to allow the one or more setscrew project into the circumferential channel to axially secure the actuator to the plunger track housing.

The tensioning device may further comprise a load cell device configured to generate signals indicative of an amount of tension force applied to a portion of the plunger. For example, the load cell can be integrated with a proximal flange portion of the plunger. In some examples, the plunger comprises a suture-attachment structure associated with a portion of the plunger that is on a proximal side of the flange portion and an elongate threaded portion that is on a distal side of the flange portion.

In some implementations, the present disclosure relates to a method for tensioning sutures. The method comprises drawing a suture through one or more channels of a suture-tensioning device, fixing the suture to a plunger component of the suture-tensioning device, and adjusting a relative axial position between the plunger component and a plunger track component of the suture-tensioning device to thereby adjust a tension of a portion of the suture.

Adjusting the relative axial position between the plunger component and the plunger track component can involve manipulating an actuator coupled to the plunger component and the plunger track component. For example, Manipulating the actuator may involve rotating the actuator about the plunger track component to thereby drive threads of the plunger component using corresponding threads of the actuator component. In some examples, fixing the suture to the plunger component involves engaging the suture with a suture-fixation feature associated with a proximal portion of the plunger component. The method can further comprise snaring the suture with a snare wire disposed in, and axially traversing, the suture-tensioning device, and drawing the suture proximally through the suture-tensioning device using the snare wire. In some examples, the method further comprises, after said adjusting the tension of the portion of the suture, clamping the suture distal to the suture-tensioning device, removing the suture-tensioning device from the suture, and tying one or more knots with the suture while the suture is clamped to fix the tension of the portion of the suture.

In some implementations, the present disclosure relates to a tensioning device comprising a plunger channel housing structure including a plurality of plunger channels therein, a plurality of elongate plungers, each of the plurality of elongate plungers being disposed at least partially within a respective one of the plurality of plunger channels, and a plurality of actuators rotatably coupled to the plunger channel housing structure, each of the plurality of actuators being configured to be actuated to cause axial displacement of a respective one of the plurality of plungers with respect to the plunger channel housing structure.

The tensioning device may further comprise a plurality of tube-access channels configured to be coupled to a respective elongate tube, wherein each of the tube-access channels is open to a respective one of the plurality of plunger channels. For example, the tensioning device may further comprise a plurality of elongate tubes each coupled to a respective one of the plurality of tube-access channels.

In some examples, the plunger channel housing structure includes a plurality of actuator engagement structures configured to be axially secured to the plurality of actuators. In some examples, the plurality of plungers each comprise one or more radially-outwardly projecting threads that circumscribe an axial length of the respective plunger and the plurality of actuators each comprise one or more radially-inwardly projecting threads configured to engage with the threads of a respective one of the plurality of plungers.

In some implementations, the present disclosure relates to a tensioning device cassette comprising a cassette structure including a plurality of bays, each of the plurality of bays being configured to receive and rotationally-secure a plunger track housing structure of a suture-tensioning device. The suture-tensioning device comprises an elongate plunger configured to fit within an axial plunger track of the plunger track housing structure and an actuator configured to drive the plunger axially within the plunger track.

The plurality of bays may be laterally arranged along at least a portion of a width dimension of the cassette structure. In some examples, adjacent bays of the plurality of bays are staggered. A first subset of the plurality of bays may be open on a topside of the cassette structure. A second subset of the plurality of bays may be open on a bottom side of the cassette structure. As an example, the plurality of bays can be arranged in a circular arrangement.

For purposes of summarizing the disclosure, certain aspects, advantages and novel features have been described. It is to be understood that not necessarily all such advantages may be achieved in accordance with any particular example. Thus, the disclosed examples may be carried out in a manner that achieves or optimizes one advantage or group of advantages as taught herein without necessarily achieving other advantages as may be taught or suggested herein.

BRIEF DESCRIPTION OF THE DRAWINGS

Various examples are depicted in the accompanying drawings for illustrative purposes and should in no way be interpreted as limiting the scope of the inventions. In addition, various features of different disclosed examples can be combined to form additional examples, which are part of this disclosure. Throughout the drawings, reference numbers may be reused to indicate correspondence between reference elements. However, it should be understood that the use of similar reference numbers in connection with multiple drawings does not necessarily imply similarity between respective examples associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some examples or configurations.

FIG. 13 shows a cross-sectional side view of a plunger track member of the suture-tensioning device shown in FIG. 12 in accordance with one or more examples.

FIG. 14 shows a proximal end view of the plunger track member shown in FIG. 13 in accordance with one or more examples.

FIG. 15 shows a side view of a plunger member of the suture-tensioning device shown in FIG. 12 in accordance with one or more examples.

FIG. 16 shows a distal end view of the plunger member shown in FIG. 15 in accordance with one or more examples.

FIGS. 20-1, 20-2, and 20-3 provide a flow diagram illustrating a process for tensioning sutures in accordance with one or more examples.

FIGS. 21-1, 21-2, and 21-3 show certain images corresponding to respective blocks, states, and/or operations associated with the process of FIG. 20 in accordance with one or more examples.

Figure 1:
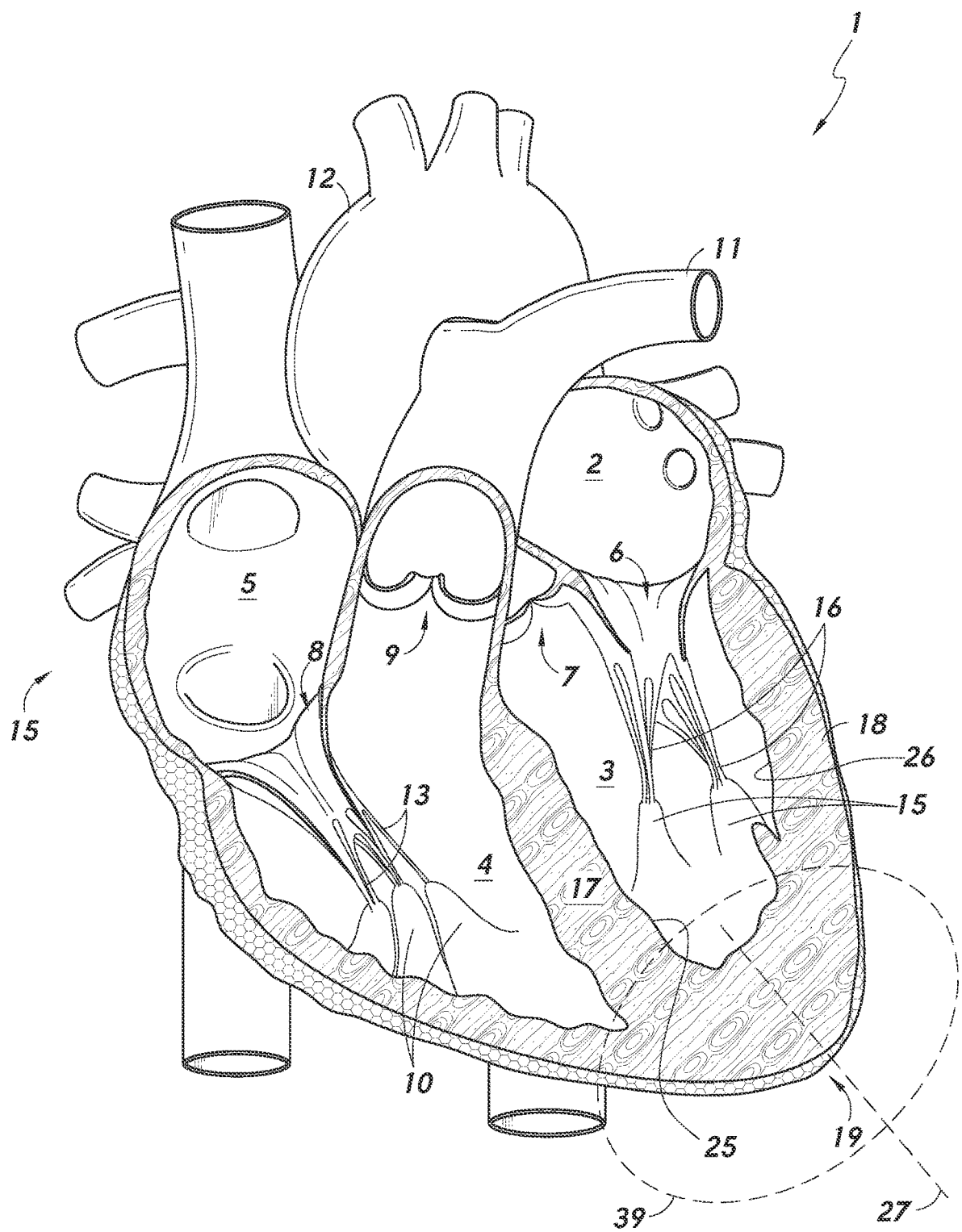
FIG. 1 is a cutaway view of the human heart.

To further clarify various aspects of examples of the present disclosure, a more particular description of certain examples will be made by reference to various aspects of the appended drawings. It is appreciated that these drawings depict only typical examples of the present disclosure and are therefore not to be considered limiting of the scope of the disclosure. Moreover, while the figures can be drawn to scale for some examples, the figures are not necessarily drawn to scale for all examples. Examples of the present disclosure will be described and explained with additional specificity and detail through the use of the accompanying drawings.

DETAILED DESCRIPTION

The following description refers to the accompanying drawings, which illustrate specific examples. Other examples having different structures and operation do not depart from the scope of the disclosure. Examples of the present disclosure relate to devices and methods for distributing and/or balancing pensions of sutures or suture portions. For example, some examples of the present disclosure relate to distribution/balancing of suture portions associated with tissue anchors (e.g., suture knots) deployed in connection with, for example, a heart valve repair procedure, such as mitral valve repair, which may be performed on a beating heart according to some implementations. With respect to delivery devices and systems used to deliver such tissue anchors, such delivery devices/systems may be referred to herein as tissue anchor delivery devices/systems and/or valve repair devices/systems.

Disclosed herein are suture-tensioning devices, which can have a generally elongate shape or form, at least in part. The devices can be used to facilitate or promote relatively precise tensioning of sutures (e.g., suture portions) anchored to biological tissue such as to one or more mitral valve leaflets. Although aspects of the present disclosure are presented in the context of sutures associated with tissue anchors (e.g., valve leaflet repair tissue anchors), it should be understood that tensioning device in accordance with the present disclosure may be used for tensioning any type of suture or other elongate form/member.

The term "suture" is used herein according to its plain and ordinary meaning and may refer to any elongate cord strip, strand, line, rope, wire, filament, tie, string, ribbon, strap, or portion thereof, or other type/form of material used in medical procedures (e.g., ePTFE suture, for example, GORE-TEX® ePTFE suture (W. L. Gore, Newark, Delaware); polyester suture, for example, ETHIBOND® polyester suture (Ethicon); polypropylene suture; ultra-high-molecular-weight polyethylene (UHMWPE) suture, for example, FORCE FIBER® suture (Teleflex); etc.). Furthermore, examples of the present disclosure may be implemented in connection with non-surgical and/or non-biological suture/line tensioning. With respect to the present disclosure, one having ordinary skill in the art will understand that a wire or other similar material may be used in place of a suture. Furthermore, in some contexts herein, the terms "cord" and "suture" may be used substantially interchangeably. In addition, use of the singular form of any of the suture-related terms listed above, including the terms "suture" and "cord," may be used to refer to a single suture/cord, or to a portion thereof. For example, where a suture knot or anchor is deployed on a distal side of a tissue portion, and where two suture portions extend from the knot/anchor on a proximal side of the tissue, either of the suture portions may be referred to as a "suture" or a "cord," regardless of whether both portions are part of a unitary suture or cord. Suture tensioning devices in accordance with aspects of the present disclosure may be utilized in methods for tensioning surgical sutures deployed in a ventricle and/or atrium of a heart. Such sutures and/or associated anchors may be introduced to the target implantation site using a minimally invasive incision, as described in greater detail below.

Suture-tensioning devices in accordance with aspects of the present disclosure may advantageously be used in beating-heart valve repair procedures (e.g., mitral valve repair, leaflet chordal repair, edge-to-edge valve leaflet repair). With respect to heart valve repair procedures, proper suture tensioning can advantageously reduce the risk of postoperative suture rupture under tension. The ability to use devices of the present disclosure in percutaneous and/or other minimally-invasive manners can reduce the amount of patient trauma, and can further allow for real-time monitoring adjustment of suture tension, thereby resulting in improved results. Furthermore, use of suture-tensioning devices in accordance with aspects of the present disclosure can allow a surgeon or other technician to control the amount of tension applied to surgical sutures and/or to ensure that implants associated therewith are in the desired location.

The following includes a general description of human cardiac anatomy that is relevant to certain inventive features and examples disclosed herein and is included to provide context for certain aspects of the present disclosure. In humans and other vertebrate animals, the heart generally comprises a muscular organ having four pumping chambers, wherein the flow thereof is at least partially controlled by various heart valves, namely, the aortic, mitral, tricuspid, and pulmonary valves. The valves may be configured to open and close in response to a pressure gradient present during various stages of the cardiac cycle (e.g., relaxation and contraction) to at least partially control the flow of blood to a respective region of the heart and/or to blood vessels (e.g., pulmonary, aorta, etc.).

FIG. 1 illustrates an example representation of a heart 1 having various features relevant to certain aspects of the present inventive disclosure. The heart 1 includes four chambers, namely the left ventricle 3, the left atrium 2, the right ventricle 4, and the right atrium 5. A wall of muscle 17, referred to as the septum, separates the left 2 and right 5 atria and the left 3 and right 4 ventricles. The inferior tip 19 of the heart 1 is referred to as the apex and is generally located on the midclavicular line, in the fifth intercostal space. The apex 19 can be considered part of the greater apical region 39.

The left ventricle 3 is the primary pumping chamber of the heart 1. A healthy left ventricle is generally conical or apical in shape in that it is longer (along a longitudinal axis extending in a direction from the aortic valve 7 to the apex 19) than it is wide (along a transverse axis extending between opposing walls 25, 26 at the widest point of the left ventricle) and descends from a base 15 with a decreasing cross-sectional circumference to the point or apex 19. Generally, the apical region 39 of the heart is a bottom region of the heart that is within the left or right ventricular region but is distal to the mitral 6 and tricuspid 8 valves and toward the tip of the heart. More specifically, the apical region 39 may be considered to be within about 20 cm to the right or to the left of the median axis 27 of the heart 1.

The pumping of blood from the left ventricle is accomplished by a squeezing motion and a twisting or torsional motion. The squeezing motion occurs between the lateral wall 18 of the left ventricle and the septum 17. The twisting motion is a result of heart muscle fibers that extend in a circular or spiral direction around the heart. When these fibers contract, they produce a gradient of angular displacements of the myocardium from the apex 19 to the base 15 about the longitudinal axis of the heart. The resultant force vectors extend at angles from about 30-60 degrees to the flow of blood through the aortic valve 7. The contraction of the heart is manifested as a counterclockwise rotation of the apex 19 relative to the base 15, when viewed from the apex 19. A healthy heart can pump blood from the left ventricle in a very efficient manner due to the spiral contractility of the heart.

The heart 1 further includes four valves for aiding the circulation of blood therein, including the tricuspid valve 8, which separates the right atrium 5 from the right ventricle 4. The tricuspid valve 8 may generally have three cusps or leaflets and may generally close during ventricular contraction (e.g., systole) and open during ventricular expansion (e.g., diastole). The valves of the heart 1 further include the pulmonary valve 9, which separates the right ventricle 4 from the pulmonary artery 11 and may be configured to open during systole so that blood may be pumped toward the lungs, and close during diastole to prevent blood from leaking back into the heart from the pulmonary artery. The pulmonary valve 9 generally has three cusps/leaflets, wherein each one may have a crescent-type shape. The heart 1 further includes the mitral valve 6, which generally has two cusps/leaflets and separates the left atrium 2 from the left ventricle 3. The mitral valve 6 may generally be configured to open during diastole so that blood in the left atrium 2 can flow into the left ventricle 3, and advantageously close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The atrioventricular (e.g., mitral and tricuspid) heart valves may comprise a collection of chordae tendineae (13, 16) and papillary muscles (10, 15) for securing the leaflets of the respective valves to promote and/or facilitate proper coaptation of the valve leaflets and prevent prolapse thereof. The papillary muscles, for example, may generally comprise finger-like projections from the ventricle wall. With respect to the tricuspid valve 8, the normal tricuspid valve may comprise three leaflets and three corresponding papillary muscles 10 (two shown in FIG. 1). The leaflets of the tricuspid valve may be referred to as the anterior, posterior and septal leaflets, respectively. The valve leaflets are connected to the papillary muscles 10 by the chordae tendineae 13, which are disposed in the right ventricle 4 along with the papillary muscles 10.

Surrounding the ventricles (3, 4) are a number of arteries (not shown) that supply oxygenated blood to the heart muscle and a number of veins that return the blood from the heart muscle. The coronary sinus (not shown) is a relatively large vein that extends generally around the upper portion of the left ventricle 3 and provides a return conduit for blood returning to the right atrium 5. The coronary sinus terminates at the coronary ostium (not shown) through which the blood enters the right atrium.

With respect to the mitral valve 6, a normal mitral valve may comprise two leaflets (anterior and posterior) and two corresponding papillary muscles 15. The papillary muscles 15 originate in the left ventricle wall and project into the left ventricle 3. Generally, the anterior leaflet may cover approximately two-thirds of the valve annulus. Although the anterior leaflet covers a greater portion of the annulus, the posterior leaflet may comprise a larger surface area in certain anatomies.

Various disease processes can impair the proper functioning of one or more of the valves of the heart. These disease processes include degenerative processes (e.g., Barlow's disease, fibroelastic deficiency), inflammatory processes (e.g., rheumatic heart disease) and infectious processes (e.g., endocarditis). Additionally, damage to the ventricle from prior heart attacks (e.g., myocardial infarction secondary to coronary artery disease) or other heart diseases (e.g., cardiomyopathy) can distort the valve's geometry causing it to dysfunction. However, the vast majority of patients undergoing valve surgery, such as mitral valve surgery, suffer from a degenerative disease that causes a malfunction in one or more leaflets of the valve which results in prolapse and regurgitation.

The mitral valve 6 and tricuspid valve 8 can be divided into three parts: an annulus, leaflets, and a sub-valvular apparatus. The sub-valvular apparatus can be considered to include the papillary muscles 10, 15 and the chordae tendineae 13, 16, which can elongate (e.g., degenerative mitral valve disease) and/or rupture. If a valve is functioning properly, when closed, the free margins or edges of the leaflets come together and form a tight junction, the are of which, in the mitral valve, is known as the line, plane or area of coaptation. Normal mitral and tricuspid valves open when the ventricles relax allowing blood from the atrium to fill the decompressed ventricle. When the ventricle contracts, the chordae tendineae advantageously properly tether or position the valve leaflets such that the increase in pressure within the ventricle causes the valve to close, thereby preventing blood from leaking into the atrium and assuring that substantially all of the blood leaving the ventricle is ejected through the aortic valve 7 or pulmonic valve 9 and into the arteries of the body. Accordingly, proper function of the valves depends on a complex interplay between the annulus, leaflets, and sub-valvular apparatus. Lesions in any of these components can cause the valve to dysfunction and thereby lead to valve regurgitation.

Generally, there are three mechanisms by which a heart valve becomes regurgitant or incompetent; they include Carpentier's type I, type II and type III malfunctions. A Carpentier type I malfunction involves the dilation of the annulus such that normally functioning leaflets are distracted from each other and fail to form a tight seal (e.g., do not coapt properly). Included in a type I mechanism malfunction are perforations of the valve leaflets, as in endocarditis. A Carpentier's type II malfunction involves prolapse of one or both leaflets above the plane of coaptation. This is the most common cause of mitral regurgitation and is often caused by the stretching or rupturing of chordae tendineae normally connected to the leaflet. A Carpentier's type III malfunction involves restriction of the motion of one or more leaflets such that the leaflets are abnormally constrained below the level of the plane of the annulus. Leaflet restriction can be caused by rheumatic disease (IIIa) or dilation of the ventricle (IIIb).

One or more chambers in the heart 1 may be accessed in accordance with certain heart valve-repair procedures and/or other interventions. Access into a chamber in the heart may be made at any suitable site of entry. In some implementations, access is made to a chamber of the heart, such as a target ventricle (e.g., left ventricle) associated with a diseased heart valve, through the apical region 39. For example, access into the left ventricle 3 (e.g., to perform a mitral valve repair) may be gained by making a relatively small incision at the apical region 39, close to (or slightly skewed toward the left of) the median axis 27 of the heart. Access into the right ventricle 4 (e.g., to perform a tricuspid valve repair) may be gained by making a small incision into the apical region 39, close to or slightly skewed toward the right of the median axis 27 of the heart. Accordingly, the ventricle can be accessed directly via the apex, or via an off-apex location that is in the apical region 39 but slightly removed from the tip/apex, such as via lateral ventricular wall, a region between the apex and the base of a papillary muscle, or even directly at the base of a papillary muscle. In some implementations, the incision made to access the appropriate ventricle of the heart is no longer than about 1 mm to about 5 cm, from about 2.5 mm to about 2.5 cm, or from about 5 mm to about 1 cm in length. When a percutaneous approach is sought, no incision into the apex region of the heart may be made, but rather access into the apical region 39 may be gained by direct needle puncture, for instance by an 18-gauge needle, through which an appropriate repair instrument can be advanced.

Certain inventive features disclosed herein relate to the tensioning of sutures and/or suture portions associated with certain heart valve repair systems and devices, and/or systems, process, and devices for repairing any other type of target organ tissue. The term "associated with" is used herein according to its broad and ordinary meaning. For example, where a first feature, element, component, device, or member is described as being "associated with" a second feature, element, component, device, or member, such description should be understood as indicating that the first feature, element, component, device, or member is physically coupled, attached, or connected to, integrated with, or otherwise physically related to the second feature, element, component, device, or member.

In some implementations, a suture-tensioning device in accordance with aspects of the present disclosure may be employed in repairing a mitral valve in a patient suffering from degenerative mitral regurgitation or other condition. In some implementations, a transapical off-pump echo-guided repair procedure is implemented in which at least part (e.g., a shaft portion/assembly) of a valve repair system is inserted in the left ventricle and steered to the surface of the diseased portion of a target mitral valve leaflet and used to deploy/implant a tissue anchor in the target leaflet.

The tissue anchor (e.g., sutureform formed into a bulky knot) may advantageously be integrated or coupled with one or more artificial/synthetic cords serving a function similar to that of chordae tendineae. Such artificial cord(s) may comprise suture(s) and/or suture tail portions associated with a knot-type tissue anchor and may comprise any suitable or desirable material, such as expanded polytetrafluoroethylene (ePTFE) or the like. Examples of the present disclosure provide solutions for tensioning sutures and/or portions thereof in a relatively fine-tuning manner using one or more suture-tensioning devices.

Certain processes for repairing a target organ tissue, such as repair of mitral valve leaflets to address mitral valve regurgitation, that may be relevant to some aspects of the present disclosure can include inserting a tissue anchor delivery device, such as a delivery device as described in PCT Application No. PCT/US2012/043761, (published as WO 2013/003228, and referred to herein as "the '761 PCT Application") and/or in PCT Application No. PCT/US2016/055170 (published as WO 2017/059426 and referred to herein as "the '170 PCT Application"), the entire disclosures of which are incorporated herein by reference, into a body and extending a distal end of the delivery device to a proximal side of the target tissue (e.g., leaflet).

The '761 PCT Application and the '170 PCT Application describe in detail methods and devices for performing non-invasive procedures to repair a cardiac valve, such as a mitral valve. Such procedures include procedures to repair regurgitation that occurs when the leaflets of the mitral valve do not coapt properly at peak contraction pressures, resulting in an undesired backflow of blood from the ventricle into the atrium. As described in the '761 PCT Application and the '170 PCT Application, after the malfunctioning cardiac valve has been assessed and the source of the malfunction verified, a corrective procedure can be performed. Various procedures can be performed in accordance with the methods described therein to effectuate a cardiac valve repair, which may depend on the specific abnormality and the tissues involved.

Figure 2:
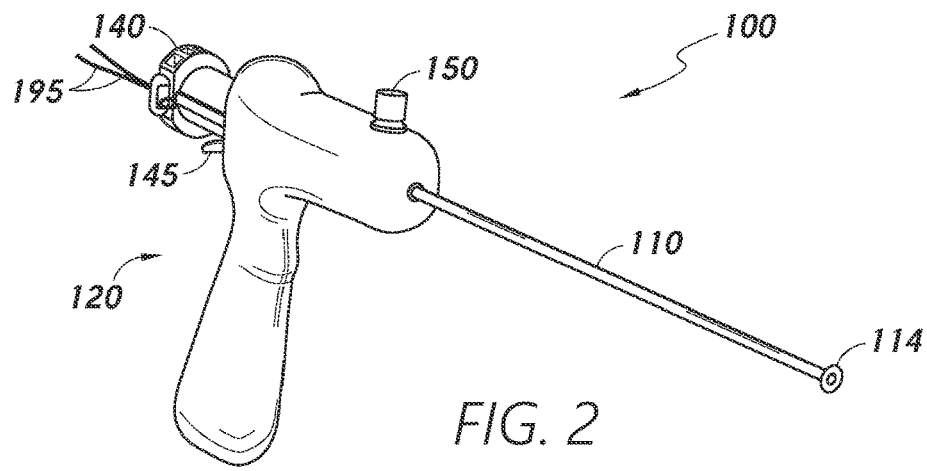
FIG. 2 is a perspective view of a tissue anchor delivery device in accordance with one or more examples.

FIG. 2 is a perspective view of a tissue anchor delivery system 100 in accordance with one or more examples. The tissue anchor delivery system 100 may be used to repair a heart valve, such as a mitral valve, and improve functionality thereof. For example, the tissue anchor delivery system 100 may be used to reduce the degree of mitral regurgitation in patients suffering from mitral regurgitation caused by, for example, midsegment prolapse of valve leaflets as a result of degenerative mitral valve disease. In order to repair such a valve, the tissue anchor delivery system 100 may be utilized to deliver and anchor tissue anchors, such as suture-knot-type tissue anchors, in a prolapsed valve leaflet. As described in detail below, such procedure may be implemented on a beating heart.

The delivery system 100 includes a rigid elongate tube 110 forming at least one internal working lumen. Although described in certain examples and/or contexts as comprising a rigid elongate tube, it should be understood that tubes, shafts, lumens, conduits, and the like disclosed herein may be either rigid, at least partially rigid, at least flexible, and/or at least partially flexible. Therefore, any such component described herein, whether or not referred to as rigid herein should be interpreted as possibly being at least partially flexible. In accordance with the present disclosure, the rigid elongate tube 110 may be referred to as a shaft for simplicity. Implementation of a valve-repair procedure utilizing the delivery system 100 can be performed in conjunction with certain imaging technology designed to provide visibility of the shaft 110 of the delivery system 100 according to a certain imaging modality, such as echo imaging. Generally, when performing a valve-repair procedure utilizing the tissue anchor delivery system 100, the operating physician may advantageously work in concert with an imaging technician, who may coordinate with the physician to facilitate successful execution of the valve-repair procedure.

In addition to the delivery shaft 110, the delivery system 100 may include a plunger feature 140, which may be used or actuated to manually deploy a pre-formed knot, such as a bulky knot as described in detail below. The tissue anchor delivery system 100 may further include a plunger lock mechanism 145, which may serve as a safety lock that locks the valve delivery system until ready for use or deployment of a leaflet anchor as described herein. The plunger 140 may have associated therewith a suture-release mechanism, which may be configured to lock in relative position a pair of suture tails 195 associated with a pre-formed knot anchor (not shown) to be deployed. For example, the suture portions 195 may be ePTFE sutures. The system 100 may further comprise a flush port 150, which may be used to de-air the lumen of the shaft 110. For example, heparinized saline flush, or the like, may be connected to the flush port 150 using a female Luer fitting to de-air the valve repair system 100. The term "lumen" is used herein according to its broad and ordinary meaning, and may refer to a physical structure forming a cavity, void, pathway, or other channel, such as an at least partially rigid elongate tubular structure, or may refer to a cavity, void, pathway, or other channel, itself, that occupies a space within an elongate structure (e.g., a tubular structure). Therefore, with respect to an elongate tubular structure, such as a shaft, tube, or the like, the term "lumen" may refer to the elongate tubular structure and/or to the channel or space within the elongate tubular structure.

The lumen of the shaft 110 may house a needle (not shown) that is wrapped at least in part with a pre-formed knot sutureform anchor, as described in detail herein. In some examples, the shaft 110 presents a relatively low profile. For example, the shaft 110 may have a diameter of approximately 3 mm or less (e.g., about 9 Fr or less). The shaft 110 is associated with an atraumatic tip 114 feature. The atraumatic tip 114 can be an echogenic leaflet-positioner component, which may be used for deployment and/or positioning of the suture-type tissue anchor. The atraumatic tip 114, disposed at the distal end of the shaft 110, may be configured to have deployed therefrom a wrapped preformed suture knot (e.g., sutureform), as described herein.

The atraumatic tip 114 may be referred to as an "end effector." In addition to a pre-formed knot sutureform and associated needle, the shaft 110 may house an elongated knot pusher tube (not shown; also referred to herein as a "pusher"), which may be actuated using the plunger 140 in some examples. As described in further detail below, the tip 114 provides a surface against which the target valve leaflet may be held in connection with deployment of a leaflet anchor.

The delivery device 100 may be used to deliver a "bulky knot" type tissue anchor, as described in greater detail below. For example, the delivery device 100 may be utilized to deliver a tissue anchor (e.g., bulky knot) on a distal side of a mitral valve leaflet. The tip 114 (e.g., end effector), can be placed in contact with a leaflet of a mitral valve. The tip 114 can be coupled to the distal end portion of the shaft 110, wherein the proximal end portion of the shaft 110 may be coupled to a handle portion 120 of the delivery device 100, as shown. Generally, the elongate pusher (not shown) may be movably disposed within a lumen of the shaft 110 and coupled to a pusher hub (not shown) that is movably disposed within the handle 120 and releasably coupled to the plunger 140. A needle (not shown) carrying a pre-formed tissue anchor sutureform can be movably disposed within a lumen of the pusher and coupled to a needle hub (not shown) that is also coupled to the plunger 140. The plunger 140 can be used to actuate or move the needle and the pusher during deployment of a distal anchor (see, e.g., FIGS. 5 and 6) and is movably disposed at least partially within the handle 120. For example, the handle 120 may define a lumen in which the plunger 140 can be moved. During operation, the pusher may also move within the lumen of the handle 120. The plunger lock 145 can be used to prevent the plunger 140 from moving within the handle 120 during storage and prior to performing a procedure to deploy a tissue anchor.

The needle may have the pre-formed knot disposed about a distal portion thereof while maintained in the shaft 110. For example, the pre-formed knot may be formed of one or more sutures configured in a coiled sutureform (see FIG. 5) having a plurality of winds/turns around the needle over a portion of the needle that is associated with a longitudinal slot in the needle that runs from the distal end thereof. Although the term "sutureform" is used herein, it should be understood that such components/forms may comprise suture, wire, or any other elongate material wrapped or formed in a desired configuration. The coiled sutureform can be provided or shipped disposed around the needle. In some examples, two suture tails extend from the coiled sutureform. The suture tails 195 may extend through the lumen of the needle and/or through a passageway of the plunger 140 and may exit the plunger 140 at a proximal end portion thereof. The coiled sutureform may advantageously be configured to be formed into a suture-type tissue anchor (referred to herein as a "bulky knot") in connection with an anchor-deployment procedure, as described in more detail below. The coiled sutureform can be configurable to a knot/deployed configuration by approximating opposite ends of the coiled portion thereof towards each other to form one or more loops.

The delivery device can further include a suture/tether catch mechanism (not shown) coupled to the plunger 140 at a proximal end of the delivery device 100, which may be configured to releasably hold or secure a suture 195 extending through the delivery device 100 during delivery of a tissue anchor as described herein. The suture catch can be used to hold the suture 195 with a friction fit or with a clamping force and can have a lock that can be released after the tissue anchor has been deployed/formed into a bulky knot, as described herein.

As described herein, the anchor delivery device 100 can be used in beating heart mitral valve repair procedures. In some examples, the shaft 110 of the delivery device 100 can be configured to extend and contract with the beating of the heart. During systolic contraction, the median axis of the heart generally shortens. For example, the distance from the apex 19 of the heart to the valve leaflets 52, 54 can vary by about 1 centimeter (cm) to about 2 centimeters (cm) with each heartbeat in some patients. In some examples, the length of the shaft 110 that protrudes from the handle 120 can change with the length of the median axis of the heart. That is, distal end of the shaft no can be configured to be floating such that the shaft can extend and retract with the beat of the heart so as to maintain contact with the target mitral valve leaflet.

Advancement of the delivery device 100 may be performed in conjunction with echo imaging, direct visualization (e.g., direct transblood visualization), and/or any other suitable remote visualization technique/modality. With respect to cardiac procedures, for example, the delivery device 100 may be advanced in conjunction with transesophageal (TEE) guidance and/or intracardiac echocardiography (ICE) guidance to facilitate and to direct the movement and proper positioning of the device for contacting the appropriate target cardiac region and/or target cardiac tissue (e.g., a valve leaflet, a valve annulus, or any other suitable cardiac tissue). Typical procedures that can be implemented using echo guidance are set forth in Suematsu, Y., *J. Thorac. Cardiovasc. Surg.* 2005; 130:1348-56 ("Suematsu"), the entire disclosure of which is incorporated herein by reference.

Figure 3:
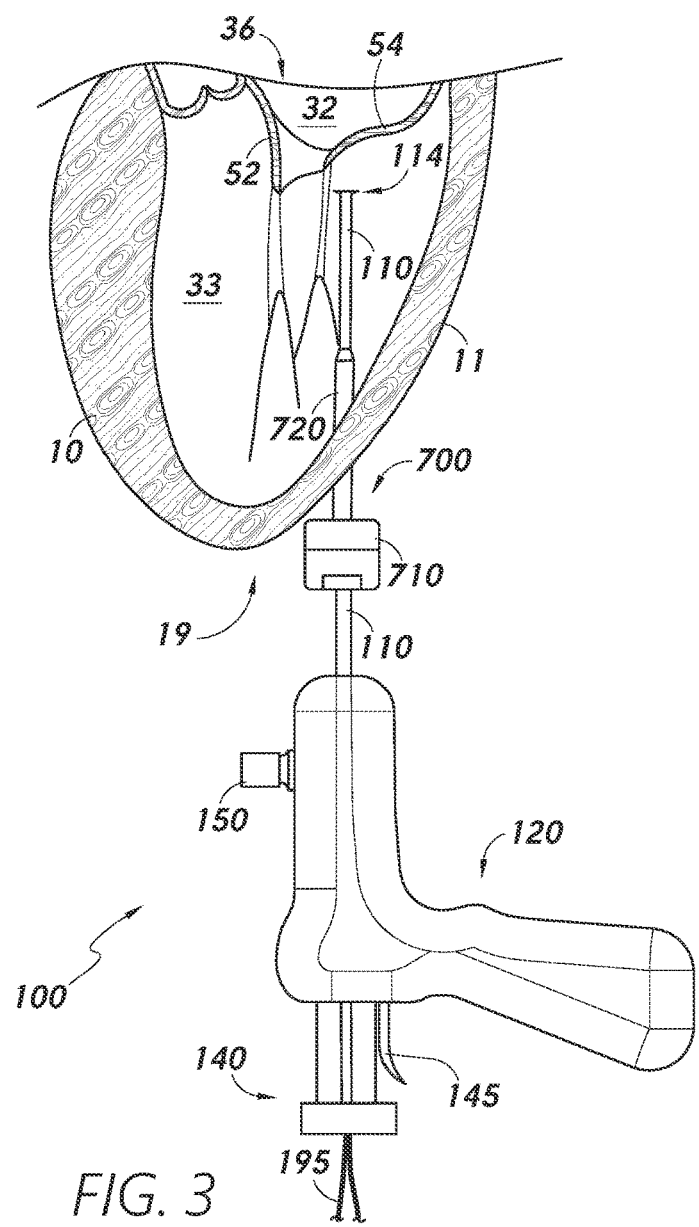
FIG. 3 is a cutaway view of a tissue anchor delivery device disposed at least partially within a chamber of a heart in accordance with one or more examples.

FIG. 3 is a cutaway view of a tissue anchor delivery device 100 disposed at least partially within a chamber of a heart in accordance with one or more examples. According to some implementations of valve-repair procedures, an incision into the apical region 39 of the appropriate ventricle 33 of the heart is made. For instance, an introducer port device 700 containing a one or more fluid-retention valves to prevent blood loss and/or air entry into the ventricle 33, may be inserted into the site of entry. Once inside the chamber 33, the shaft no of the delivery device 100 may be advanced through the lumen 720 of the introducer 700. In some examples, a sheath may be inserted through the introducer 700, through which one or more other instruments are advanced. For instance, an endoscope may first be advanced into the chamber 33 to visualize the ventricle, the valve 36, and/or the sub-valvular apparatus. By use of an appropriate endoscope, a careful analysis of the malfunctioning valve 36 may be performed. Each segment of each leaflet may be carefully assessed to determine its pliability, integrity, and motion. Based on this assessment, the practitioner can determine whether the valve can indeed be repaired or must be replaced. The motion of the leaflets 52, 54 can be classified as slightly dysfunctional, prolapsed, or restricted and based on this classification, the necessary steps of the repair can be determined.

Mitral valve regurgitation generally increases the workload on the heart and may lead to very serious conditions if left untreated, such as decreased ventricular function, pulmonary hypertension, congestive heart failure, permanent heart damage, cardiac arrest, and ultimately death. Since the left heart is primarily responsible for circulating the flow of blood throughout the body, malfunction of the mitral valve 36 is particularly problematic and often life threatening. Methods and devices are provided herein, as well as in the '761 PCT Application and the '170 PCT Application, for performing non-invasive procedures to repair a cardiac valve, such as a mitral valve. Such procedures include procedures to repair regurgitation that occurs when the leaflets of the mitral valve do not coapt properly at peak contraction pressures, resulting in an undesired backflow of blood from the ventricle into the atrium. As described in the '761 PCT Application and the '170 PCT Application, after the malfunctioning cardiac valve has been assessed and the source of the malfunction verified, a corrective procedure can be performed. Various procedures can be performed in accordance with the methods described therein to effectuate a cardiac valve repair, which will depend on the specific abnormality and the tissues involved.

After a minimally invasive approach is determined to be advisable, one or more incisions may be made proximate to the thoracic cavity to provide a surgical field of access. The total number and length of the incisions to be made depend on the number and types of the instruments to be used as well as the procedure(s) to be performed. The incision(s) may advantageously be made in such a manner as to be minimally invasive. As referred to herein, the term "minimally invasive" means in a manner by which an interior organ or tissue may be accessed with relatively little damage being done to the anatomical structure through which entry is sought. For example, a minimally invasive procedure may involve accessing a body cavity by a small incision/opening of, for example, approximately 5 cm or less made in the skin of the body. The incision may be vertical, horizontal, or slightly curved. If the incision is located along one or more ribs, it may advantageously follow the outline of the rib. The opening may advantageously extend deep enough to allow access to the thoracic cavity between the ribs or under the sternum and is preferably set close to the rib cage and/or diaphragm, dependent on the entry point chosen.

In one example method, the heart may be accessed through one or more openings made by one or more small incision in a portion of the body proximal to the thoracic cavity, such as between one or more of the ribs of the rib cage of a patient, proximate to the xyphoid appendage, or via the abdomen and diaphragm. Access to the thoracic cavity may be sought to allow the insertion and use of one or more thorascopic instruments, while access to the abdomen may be sought to allow the insertion and use of one or more laparoscopic instruments. Insertion of one or more visualizing instruments may then be followed by transdiaphragmatic access to the heart. Additionally, access to the heart may be gained by direct puncture (e.g., via an appropriately sized needle, for instance an 18-gauge needle) of the heart from the xyphoid region. Accordingly, the one or more incisions should be made in such a manner as to provide an appropriate surgical field and access site to the heart in the least invasive manner possible. Access may also be achieved using percutaneous methods, further reducing the invasiveness of the procedure. See, e.g., "Full-Spectrum Cardiac Surgery Through a Minimal Incision Mini-Sternotomy (Lower Half) Technique," Doty et al., *Annals of Thoracic Surgery* 1998; 65(2): 573-7 and "Transxiphoid Approach Without Median Sternotomy for the Repair of Atrial Septal Defects," Barbero-Marcial et al., *Annals of Thoracic Surgery* 1998; 65(3): 771-4, the entire disclosures of each, which are incorporated herein by reference for all purposes.

Generally, the shaft 110 of the tissue anchor delivery device 100 may be slowly advanced into the introducer 700 until the tip 114 is distal to the introducer 700 and/or cannula tip 730 thereof and entered the ventricle 33. In so doing, it may be desirable to advance the shaft 110 within the ventricle 33 in such a way as to avoid traversing areas populated by papillary muscles and/or associated chordae tendineae to avoid entanglement therewith. In order to facilitate or ensure avoidance of such anatomy, imaging technology may advantageously be implemented to provide at least partial visibility of the shaft 110 within the ventricle 33, as well as certain anatomical features within the ventricle. In some implementations, hybrid imaging technologies may be used, wherein echo imaging is used in combination with a different imaging modality. Multi-imaging modalities may provide improved visibility of anatomical and/or delivery system components.

Although the procedures described herein are with reference to repairing a cardiac mitral valve or tricuspid valve by the implantation of one or more leaflet anchors and associated suture(s)/cord(s), the methods presented are readily adaptable for various types of tissue, leaflet, and annular repair procedures. The methods described herein, for example, can be performed to selectively approximate two or more portions of tissue to limit a gap between the portions. That is, in general, the methods herein are described with reference to a mitral valve but should not be understood to be limited to procedures involving a mitral valve. Furthermore, aspects of the present disclosure applicable to non-biological structures and devices. For example, other cord or suture tensioning applications not involving biological tissue may incorporate aspects of the pension balancing and/or distribution devices, systems, and processes disclosed herein.

Figure 4:
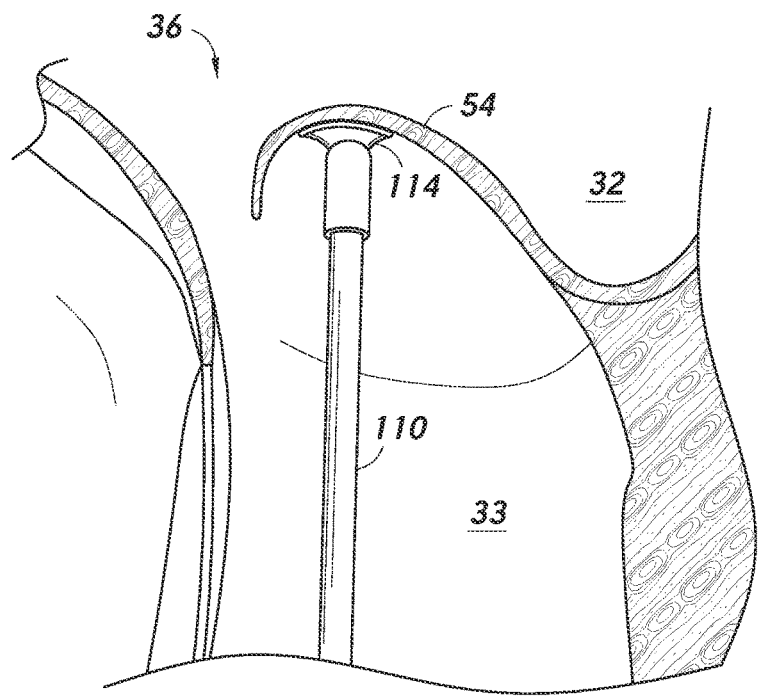
FIG. 4 is a close-up view of a distal portion of a tissue anchor delivery device shaft assembly positioned against a target heart valve leaflet in accordance with one or more examples.

FIG. 4 shows a close-up view of a shaft 110 of a tissue anchor delivery device 100 inserted into a ventricle 33 (e.g., left ventricle) and approximated to a target valve leaflet 54 in connection with a valve-repair procedure in accordance with one or more examples of the present disclosure. For example, the valve 36 may be a mitral valve. The anchor delivery device shaft 110 can be configured to deliver a tissue anchor (not shown; see, e.g., FIGS. 5-7), such as a bulky knot, to the valve leaflet 54. As an example, FIG. 4 shows a valve leaflet 54, which may represent a posterolateral leaflet of a mitral valve. It will be understood that the anchor delivery device shaft 110 can also deliver a tissue anchor to the anteromedial mitral valve leaflet. Although the description of FIGS. 4-7 below is presented in the context of a mitral valve, it should be understood that the principles disclosed herein are applicable to other valves or biological tissues, such as a tricuspid valve.

With reference to FIGS. 4-7, the anchor delivery device shaft 110 can comprise one or more elongate lumens configured to allow delivery of the anchor 190 to the valve leaflet 54. The shaft 110 can be configured to facilitate performance of one or more functions, such as grasping, suctioning, irrigating, cutting, suturing, or otherwise engaging a valve leaflet. The distal end, or tip, 114 of the shaft 110 can be configured to contact the mitral valve leaflet 54 without substantially damaging the leaflet to facilitate repair of the valve 36. For example, during a valve-repair procedure, a handle (e.g., handle 120) coupled to the shaft 110 can be manipulated in such a manner so that the leaflet 54 is contacted with the functional distal portion of the shaft 110 and a repair effectuated.

Echo imaging guidance, such as transesophageal echocardiogram (TEE) (2D and/or 3D), transthoracic echocardiogram (TTE), and/or intracardiac echo (ICE), may be used to assist in the advancement and desired positioning of the anchor delivery device shaft 110 within the ventricle 33. The distal end 114 of the shaft 110 can contact a proximal surface (e.g., underside surface with respect to the illustrated orientation of FIGS. 4-7) of the mitral valve leaflet 54, without or substantially without damaging the leaflet 54. For example, the end/tip portion or component 114 can have a relatively blunt form or configuration. The end/tip portion or component 114 can be configured to maintain contact with the proximal side of the valve leaflet 54 as the heart beats to facilitate reliable delivery of the anchor 191/190 to the target site on the leaflet 54.

Figure 5:
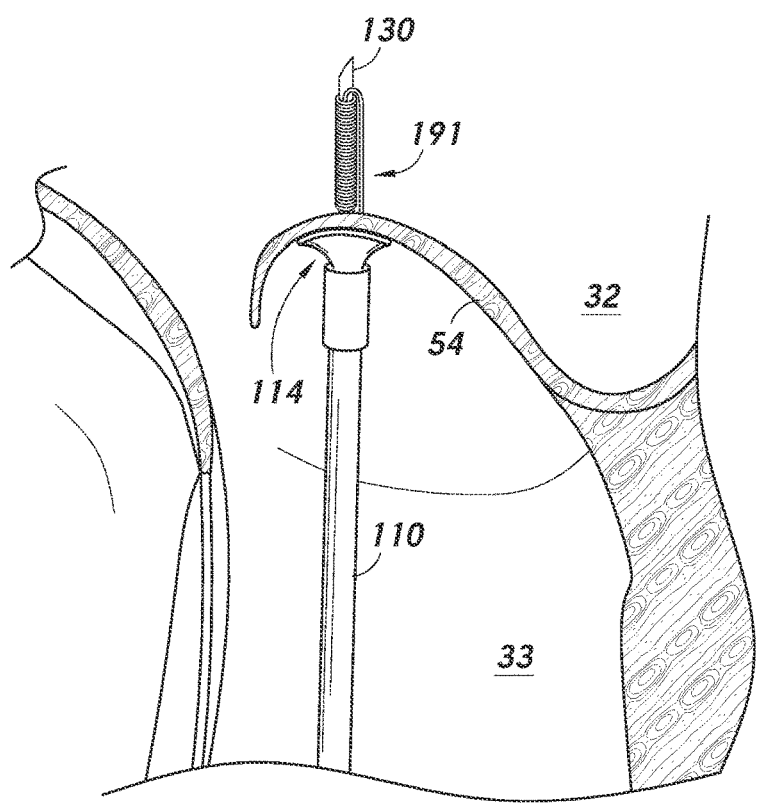
FIG. 5 is a close-up view of a distal portion of a tissue anchor delivery device shaft having a needle and tissue anchor sutureform projected therefrom through a target heart valve leaflet in accordance with one or more examples.
Figure 6:
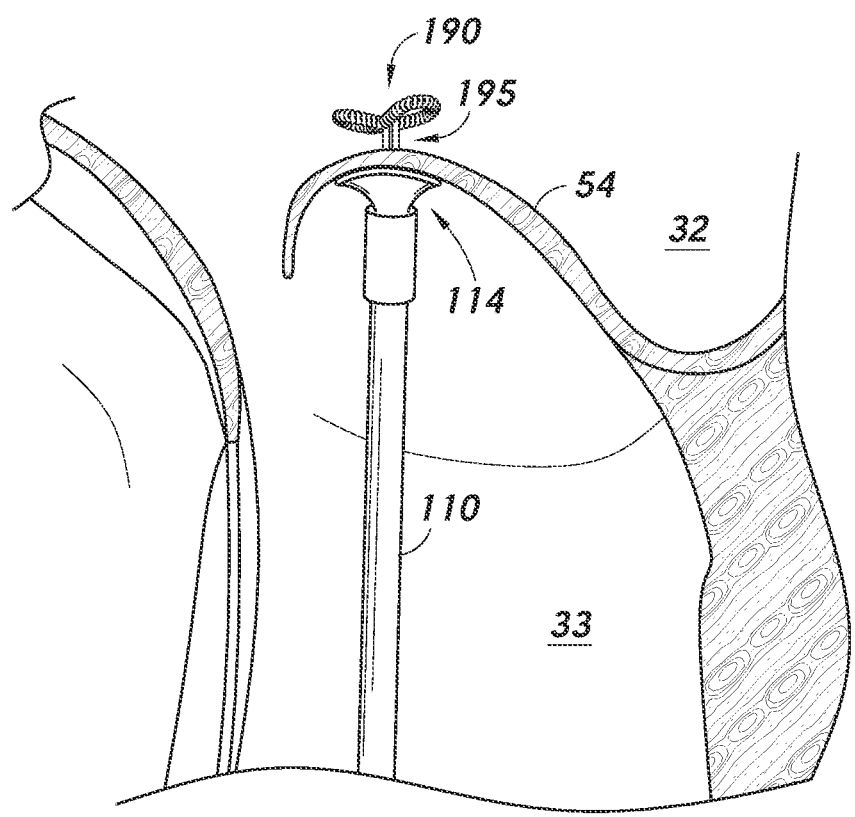
FIG. 6 is a close-up view of a distal portion of a tissue anchor delivery device shaft assembly positioned against a target heart valve leaflet and an associated tissue anchor deployed on a distal side of the leaflet in accordance with one or more examples.
Figure 7:
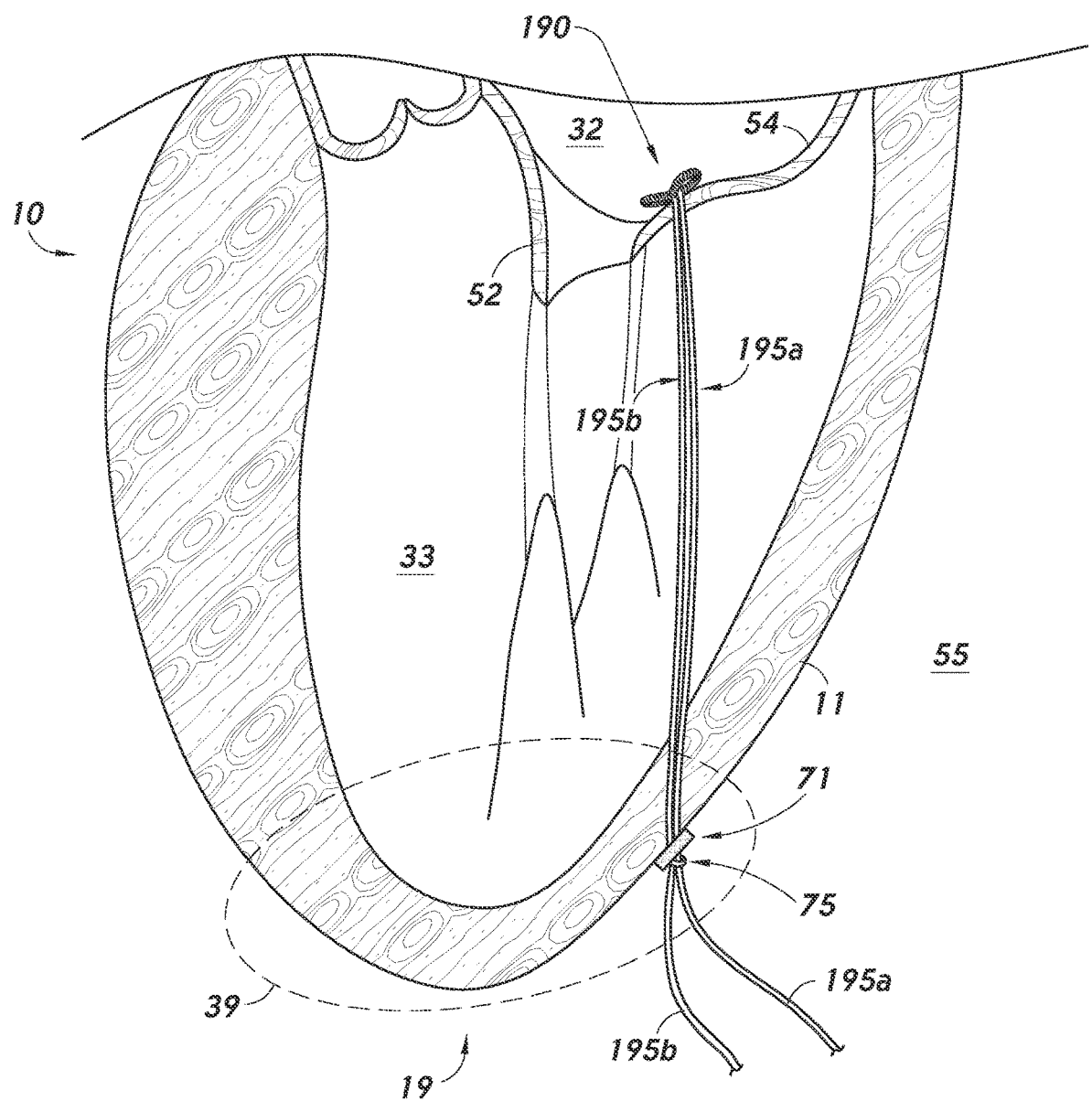
FIG. 7 shows a cutaway view of a deployed leaflet anchor in a heart in accordance with one or more examples.

In some examples, one or more perforation devices 130 (e.g., needle(s)) can be delivered through a working lumen (not shown) of the shaft 110 to the valve leaflet 54 to puncture the valve leaflet 54 and project a sutureform 191 including a plurality of windings of suture about a distal portion of a needle 130 into the atrium 32 (see FIG. 5), wherein the sutureform is deployed to form the bulky knot tissue anchor 190 shown in FIGS. 6 and 7. For example, as shown in FIG. 5, a slotted needle 130 can be deployed from the distal end of the shaft 110, thereby puncturing the leaflet 54 and projecting into the atrium 32, wherein the slotted needle 130 is wrapped with a sutureform 191 (e.g., ePTFE suture) in a particular configuration (see the '761 PCT Application for further detail regarding example suture wrapping configurations and needles for use in suture anchor deployment devices and methods). In some examples, a pusher or hollow guide wire (not shown) is provided on or at least partially around the needle 130 within the shaft 110, such that the needle may be withdrawn, leaving the pusher and wound sutureform 191. When a withdrawal force is applied to the sutureform 191 using the pusher, the sutureform 191 may form a bulky-knot-type anchor (e.g., the anchor 190), after which the pusher may be withdrawn, leaving the permanent knot 190 to anchor the suture(s) 195 to the leaflet 54.

FIG. 4 shows the shaft 110 of the tissue anchor delivery device 100 positioned on the target valve leaflet 54 (e.g., mitral valve leaflet). For example, the target site of the valve 54 may be slowly approached from the ventricle side thereof by advancing the distal end of the shaft 110 along or near to the posterior wall of the ventricle 33 (e.g., left ventricle) without contacting the ventricle wall. Successful targeting and contacting of the target location on the leaflet 54 can depend at least in part on accurate visualization of the shaft 110 and/or tip/end effector 114 throughout the process of advancing the tip 114 to the target site. Generally, echocardiographic equipment may be used to provide the necessary or desired intra-operative visualization of the shaft 110 and/or tip 114.

Once the tip 114 is positioned in the desired position, the distal end of the shaft 110 and the tip 114 may be used to drape, or "tent," the leaflet 54 to better secure the tip 114 in the desired position, as shown in FIG. 4. Draping/tenting may advantageously facilitate contact of the tip 114 with the leaflet 54 throughout one or more cardiac cycles, to thereby provide more secure or proper deployment of leaflet anchor(s). The target location may advantageously be located relatively close to the free edge of the target leaflet 54 to minimize the likelihood of undesirable intra-atrial wall deployment of the anchor. Navigation of the tip 114 to the desired location on the underside of the target valve leaflet 54 may be assisted using echo imaging, which may be relied upon to confirm correct positioning of the tip 114 prior to anchor/knot deployment.

With the shaft 110 positioned against the target leaflet 54, the plunger 140 of the tissue anchor delivery device 100 can be actuated to move the needle 130 and a pusher disposed within the shaft 110, such that the coiled sutureform portion 191 of the suture anchor slides off the needle 130, as shown in FIG. 5. As the plunger 140 is actuated, a distal piercing portion of the needle 130 punctures the leaflet 54 and forms an opening in the leaflet. FIG. 5 shows a close-up view of the distal portion of the delivery device shaft 110 showing the needle 130 and tissue anchor sutureform 191 projected therefrom through the target leaflet 54 in accordance with one or more examples. In some examples, the needle 130 is projected a distance of between about 0.2-0.3 inches (about 5-8 mm), or less, distally beyond the distal end of the shaft 130 (e.g., beyond the tip 114). In some examples, the needle 130 is projected a distance of between about 0.15-0.4 inches (about 4-10 mm). In some examples, the needle 130 is projected a distance of about 1 inch (about 25 mm), or greater. In some examples, the needle 130 extends until the distal tip of the needle and the entire coiled sutureform 191 extend through the leaflet 54. While the needle 130 and sutureform 191 are projected into the atrial side 32 of the leaflet 54, the shaft 110 and tip 114 advantageously remain entirely on the ventricular side 33 of the leaflet 54.

As the pusher (not shown) within the tissue anchor delivery device shaft 110 is moved distally, a distal end of the pusher advantageously moves or pushes the distal coiled sutureform 191 (e.g., pre-deployment coiled portion of the suture anchor) over the distal end of the needle 130 and further within the atrium 32 of the heart on a distal side of the leaflet 54, such that the sutureform extends distally beyond a distal end of the needle 130. For example, in some examples, at least half a length of the sutureform 191 extends beyond the distal end of the needle 130. In some examples, at least three quarters of the length of the sutureform 191 extends beyond the distal end of the needle 130. In some examples, the entire coiled sutureform 191 extends beyond the distal end of the needle 130.

After the sutureform 191 has been pushed off the needle 130, pulling one or more of the suture tail(s) 195 (e.g., suture strands extending from the coiled portion of the suture) associated with the tissue anchor 190 proximally can cause the sutureform 191 to form a bulky knot anchor 190, as shown in FIG. 6, which provides a close-up view of the formed suture anchor 190 on the atrial side 32 of the leaflet 54. For example, the bulky knot suture anchor 190 may be formed by approximating opposite ends of the coils of the sutureform 191 (see FIG. 5) towards each other to form one or more loops. After the sutureform 191 has been formed into the bulky knot 190, the delivery device 100 can be withdrawn proximally, leaving the tissue anchor 190 disposed on the distal atrial side of the leaflet 54, as shown in FIG. 7. In some examples, two suture tails 195 may extend from the proximal/ventricle side 33 of the leaflet 54 and out of the heart 10. For example, the delivery device shaft 110 can be slid/withdrawn over the suture tail(s) 195. The suture tails can be advantageously be tensioned in a balanced manner according to aspects of the present disclosure.

FIG. 7 shows a cutaway view of the deployed leaflet anchor 190 in accordance with one or more examples of the present disclosure. The suture tails 195 coupled to the anchor 190 may be secured at the desired tension using a pledget 71 or other suture-fixing/locking device or mechanism on the outside of the heart through which the suture tails 195 may pass. For example, a suture tension distribution and/or balancing device in accordance with examples of the present disclosure may be utilized in addition to, or instead of, the pledget 71 for securing and/or tensioning the suture tails 195. Furthermore, one or more knots (e.g., a knot stack) or other suture fixation mechanism(s) or device(s)

may be implemented to hold the sutures at the desired tension and to the pledget/device 71. With the suture tail(s) 195 fixed to the ventricle wall 11, a ventricular portion of the suture tail(s) 195 may advantageously function as replacement leaflet cords (e.g., chordae tendineae) that are configured to tether the target leaflet 54 in a desired manner and at a desired tension.

Figure 8:
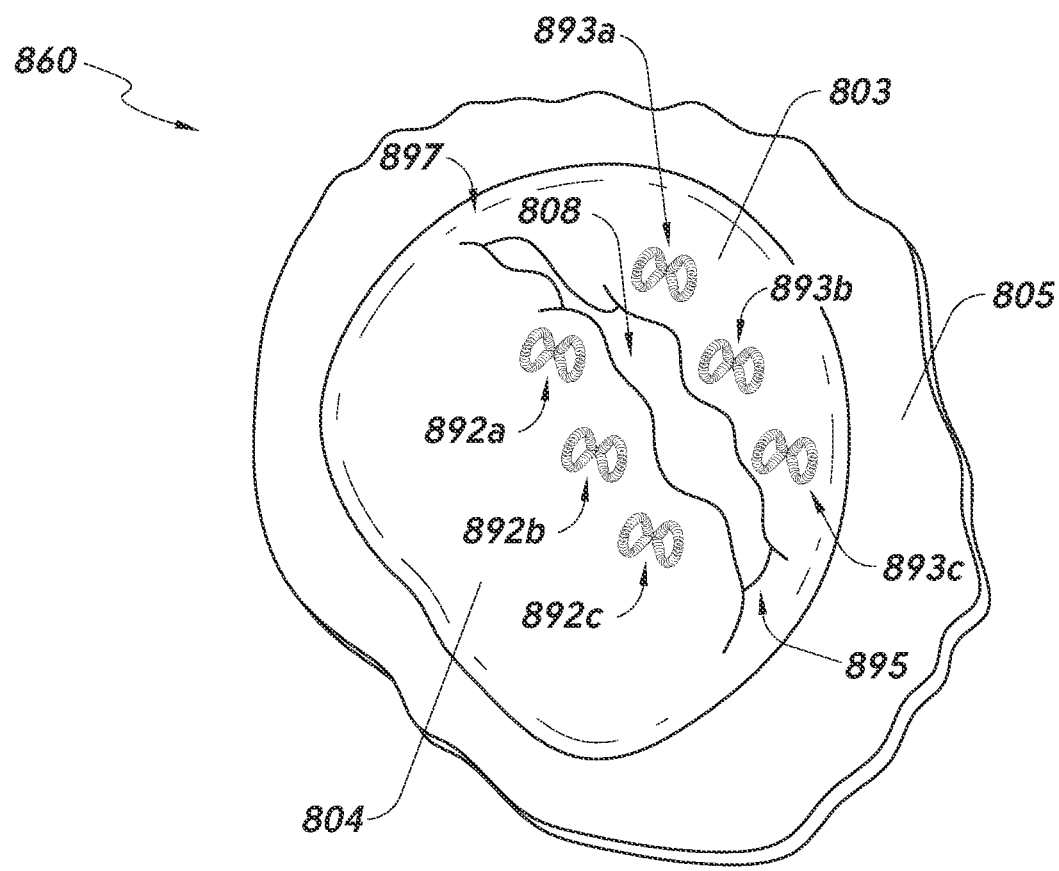
FIG. 8 shows a top view of a heart valve with leaflets having a plurality of tissue anchors implanted therein in accordance with one or more examples.

FIG. 8 shows a top view of a heart valve 860 with leaflets 803, 804 having a plurality of tissue anchors 892, 893 implanted therein in accordance with one or more examples. For example, the heart valve 860 may be a mitral valve, tricuspid valve, or other type of valve or tissue. That is, although certain description is presented below describing a mitral valve, it should be understood that such description is for simplicity and clarity only, and the principles disclosed herein are applicable to other types of tissue or anatomy.

With respect to mitral valve repair procedures, the heart valve 860 may be considered to include an anterior leaflet 804 and a posterior leaflet 803. The leaflets 803, 804 may be joined at anterior 895 and posterior 897 commissure regions, respectively. In some implementations, one or more tissue anchors 892, 893 may be deployed in one or both of the leaflets 803, 804. For example, one or more tissue anchors 892 may be implanted in one or more of the A1, A2, and/or A3 regions (not labeled in FIG. 8 for clarity; generally numbered from lateral to medial) of the anterior leaflet 804. Additionally or alternatively, one or more tissue anchors 893 may be implanted in one or more of the P1, P2, and/or P3 regions (not labeled in FIG. 8 for clarity; generally numbered from lateral to medial) of the posterior leaflet 803. The deployed leaflet anchors may generally be below the surface of coaptation. With respect to posterior mitral valve leaflet repair, the anterior leaflet may advantageously touch the posterior leaflet basal to the leaflet anchor(s).

Each of the various tissue anchors shown in FIG. 8 may be associated with one or more suture tails, which may be referred to a suture portions in certain contexts herein. For example, in some implementations, the tissue anchors 892, 893 comprise suture forms in the form of a knot, or the like. For example, single unitary sutures may be respectively formed into the illustrated tissue anchor knots, wherein tail portions associated with the sutures/knots run from the knots to another anchor point, such as an anchor point on an outside ventricle wall or surface as shown in FIG. 7. Although certain examples are described herein in connection with pairs of suture tails associated with a respective tissue anchor, in some examples a single suture tail/portion may be associated with a single tissue anchor. Furthermore, it should be understood that suture tensioning devices and methods disclosed herein, regardless of whether such description references single suture portions or pairs of suture portions or any other number of suture portions/tails, are applicable to tension balancing and/or distribution of any number of suture portions, including single suture tails and pairs of suture tails associated with a single tissue anchor.

Suture Tensioning

Figure 9:
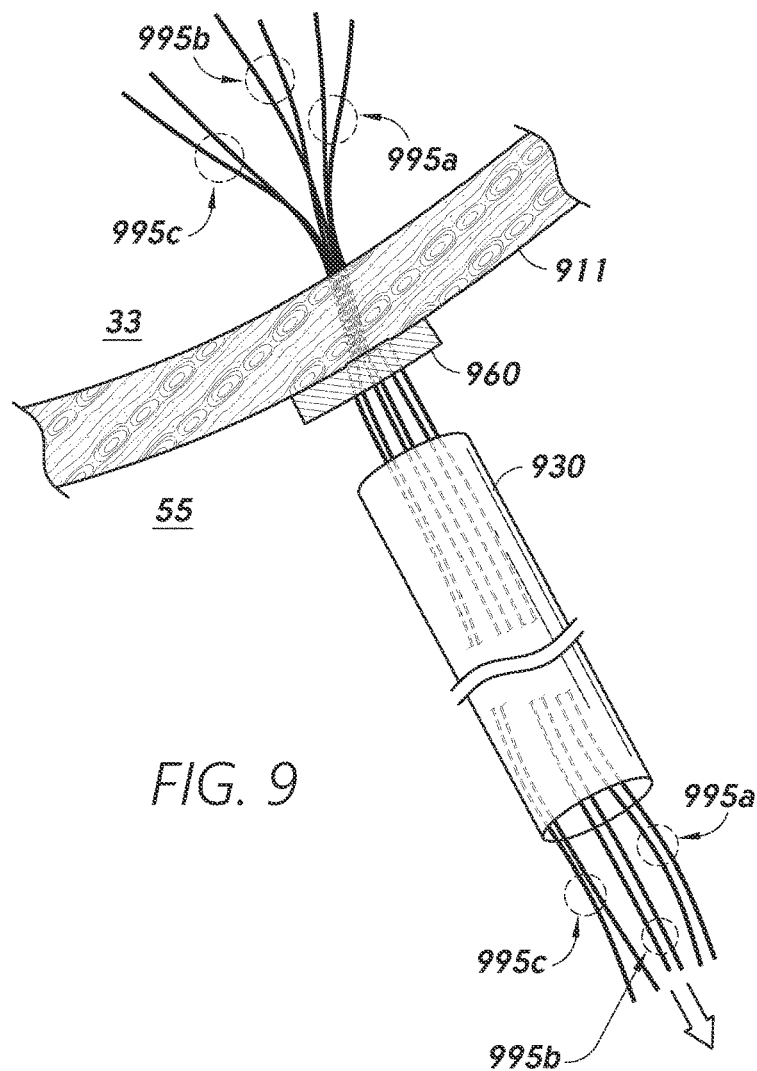
FIG. 9 shows a plurality of suture pairs passing through a cardiac tissue wall, pledget, and tourniquet in accordance with one or more examples.

Examples of the present disclosure provide solutions for achieving relatively precise tension levels for one or more of suture tails/portions and/or pairs of suture tails/portions. FIG. 9 shows a plurality of suture pairs 995 passing through a cardiac tissue wall 911 and through a tourniquet 930 in accordance with one or more examples. In some implementations, one or more leaflet anchors is deployed in each of the mitral valve leaflets, wherein sutures/cords coupled to separate leaflets are secured together in the heart by tying them together with knots or by another suitable attachment device, creating an edge-to-edge repair to decrease the septal-lateral distance of the mitral valve orifice.

According to some processes, tensioning of the suture portions 995 is performed after the placement of the associated tissue anchors in respective target tissue. With the sutures 995 pulled/passed through the ventricle wall 911, the ends of the sutures may be pulled manually to remove slack in the sutures 995. Generally, tensioning of the sutures 95 may not be performed prior to such slack-removal. Once some or all of the slack is taken out of the individual sutures and/or suture pairs, the sutures 995 can be pulled simultaneously to further increase the tension thereon (or let tension out). The sutures 995 can be pulled together through the tourniquet 930. For example, the sutures 995 can be pulled from proximal end portions thereof to achieve the determined/desired tension.

In some implementations, suture tensioning and/or fixing can be performed using the pledget 960 or other type of device through which the suture portions 995 may be passed and/or to which the suture portions can be secured, such as by tying one or more knots, or the like (see FIG. 1). For example, as shown in FIG. 9, the suture pairs 995a, 995b, 995c, each of which may be associated with a separate tissue anchor (e.g., heart valve leaflet tissue anchor), can pass through the tissue wall 911, which may be, for example, a ventricle wall associated a ventricle 33 or other area/chamber of a patient. The suture portions 995 may further be passed through a pledget device 960, which may serve at least in part to provide a buffer between the proximal suture portions/knots and the tissue wall 911.

Knots can be tied on the long free ends of the sutures 995 outside of the heart prior to placement of the pledget 960. The suture portions 995 can be identified as pairs (995a, 995b, 995c) by their respective associated knots. In some implementations, the pairs of sutures can be separated out into the two strands of the pair and put through a pledget 960. A French-eye needle may be used to pull the sutures through the pledget 960. The pairs of sutures can be identified on the proximal side of the pledget 960 based on the locations through which they exit the pledget 960. The tourniquet 930 may interface against the ventricle wall 911, with the pledget 960 positioned between the tourniquet 930 and the tissue wall 911.

The pledget 960 can be, for example, a low-porosity and relatively stiff pledget. Such a pledget may advantageously allow for the desired tension of the suture tails 995 to be sustained over an extended postoperative period of time. In some examples, suture tying or fixation may be implemented using one or more soft tissue retractors and/or right-angle clamps (not shown), which may be rubber shod to reduce the risk of damage to the suture portions 995.

In certain implementations, testing of location and/or tension of the tissue anchors and/or associated suture tail(s) 995 may be performed by gently tensioning the suture tails until leaflet motion is felt and/or observed. Echo imaging technology may be used to view and verify the anchor placement and resulting leaflet function. The steps and processes outlined above for placing a suture-knot-type tissue anchors may be repeated as necessary until the desired number of anchors have been implanted on the target valve leaflet.

In some implementations, tension adjustment in the pairs of suture tails 995 associated with multiple tissue (e.g., leaflet) anchors may be performed simultaneously. The appropriate number of leaflet anchors may advantageously be determined to produce the desired coaptation of the target valve leaflets. The pledget 960 may be drawn against the surface (e.g., epicardial surface) of the tissue wall 911, and all the suture tails 995 may be inserted through a common tourniquet 930 or like structure so that all suture portions/tails can be tensioned together.

Figure 10:
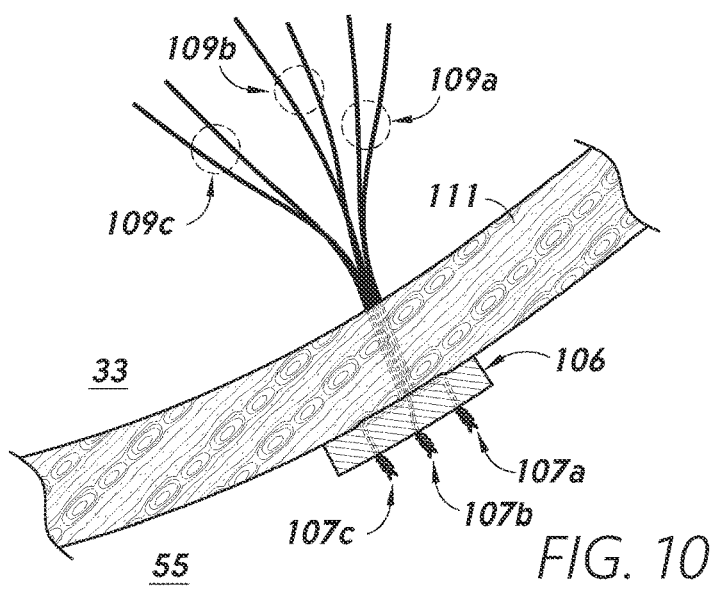
FIG. 10 shows a plurality of suture pairs passing through a cardiac tissue wall and knotted on a pledget in accordance with one or more examples.

FIG. 10 shows a plurality of suture pairs 109 passing through a cardiac tissue wall 111 and knotted on a pledget 106 in accordance with one or more examples. As shown, in some implementations, suture tails may be knotted together on a proximal side of the tissue wall 111. For example, two suture tails emanating from a common tissue anchor may be knotted together against the pledget 106. Knotting together of suture portions in accordance with aspects of the present disclosure may involve forming a knot stack 107, wherein multiple knots are tied in succession using a single pair of suture tails, or pairs of pairs the suture tails, in order to provide improved fixation and/or reduce the likelihood of the not becoming undone postoperatively.

In some implementations, the present disclosure relates to devices and methods used to tension sutures, such as artificial chordae in connection with a heart valve repair procedure. In accordance with some solutions, sutures can be hand-gripped, wherein the movements of the mitral leaflets are allowed to tug on the sutures to balance the load. However, such tensioning solutions may not allow for sufficiently controlled and/or fine-tuning of suture tension, or fine-tuning of tension in a sufficiently simple manner. In some implementations, the present disclosure provides solutions for relatively simply and precisely tensioning sutures using one or more suture-tensioning devices as described herein.

Tensioning Devices

In some implementations, the present disclosure relates to devices configured to facilitate tensioning of sutures. Generally, the amount of suture tension can be understood to be non-linear with respect to the amount of tensioning force applied thereto. Therefore, for certain manual tensioning solutions, the human operator may be prone to over-tension the relevant sutures, thereby resulting in undesired physiological effects. Furthermore, in some implementations, monitoring of suture tension may be performed under echo guidance. For example, the relevant surgeon/technician may tension sutures/cords of a valve-repair implant while monitoring the effect thereof with respect to correction of mitral regurgitation. Although some solutions provide for manual tensioning based on echo visibility and communication between the surgeon and the echocardiographer, such processes may require the surgeon to hold the tension position relatively still until the decision is made on the appropriate amounts of tensioning. Therefore, the use of a device that is configured to hold a set amount of tension without requiring the surgeon to hold such tension can be less burdensome and divide greater consistency in results compared to certain other solutions.

Figure 11:
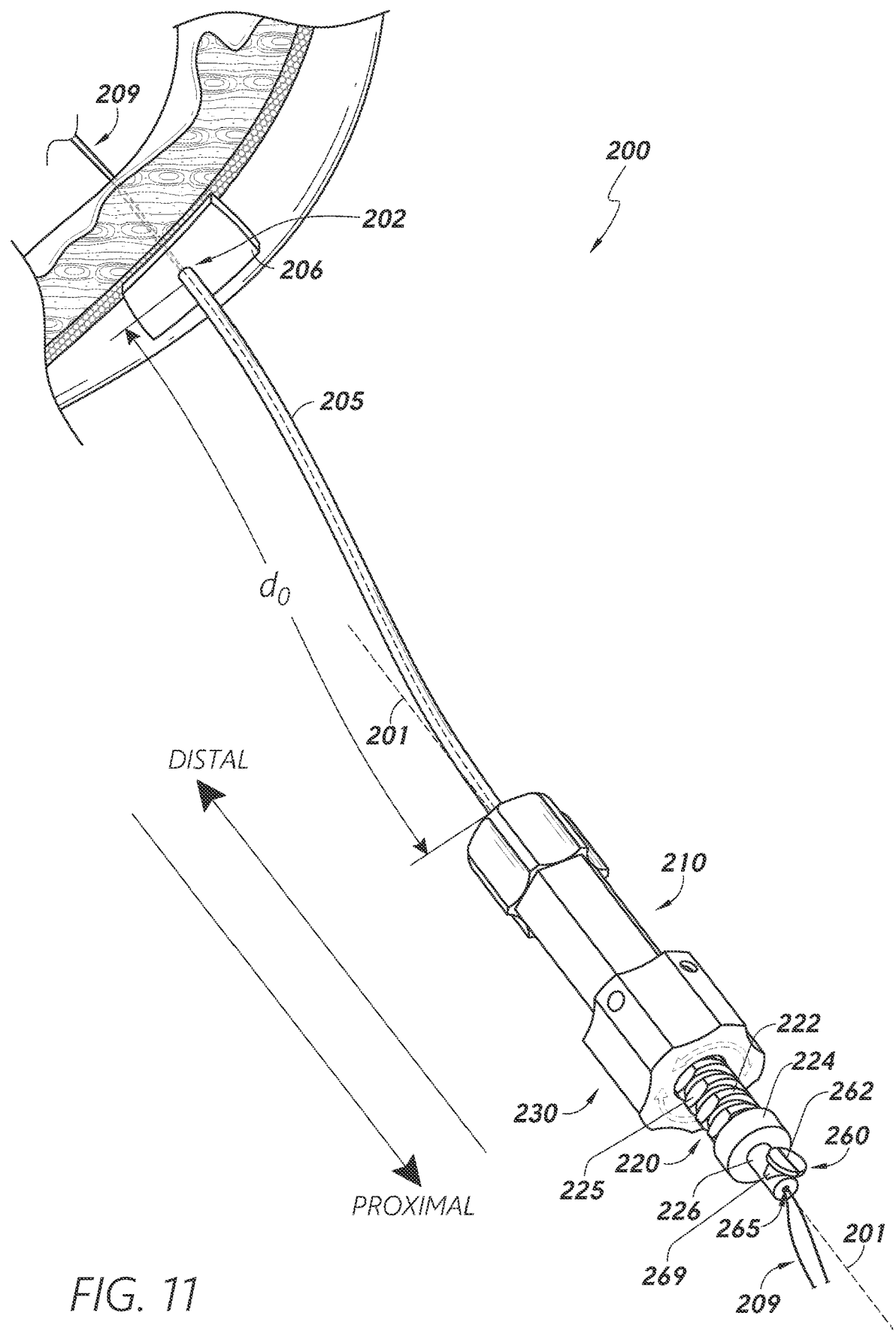
FIG. 11 shows a perspective view of a suture-tensioning device having one or more suture portions disposed at least partially therein in accordance with one or more examples.

FIG. 11 shows a perspective view of a suture-tensioning device 200 having one or more suture portions 209 disposed at least partially therein in accordance with one or more examples. The suture-tensioning device 200 is configured to control, at least in part, the amount of tension applied on the sutures 209 to thereby position tissue anchors/implants associated therewith in the desired position. For example, as shown in FIG. 11, the device 200 may have the one or more sutures 209 (e.g., one or more suture pairs) drawn through one or more channels thereof, described in detail below.

The device 200 includes a plunger member 220 configured to be axially translated along a longitudinal and/or central axis 201 of the device 200. The plunger member 220 may comprise a suture-fixation component 260, which may advantageously allow for the suture(s) 209 to be attached or fixed to the plunger member 220, such as at or near a proximal end of the anchor member 220. In some examples, the suture-fixation component 260 comprises a radially-projecting form/arm (e.g., the structure 269) configured, shaped, and/or dimensioned to have suture(s) wrapped thereabout.

The device 200 may further comprise and/or be at attached or coupled to an axially-rigid tube 205. The term "axially-rigid" is used herein according to its broad and ordinary meaning, and may refer to a characteristic of an elongate tube having a central axis, wherein the tube comprises material that does not axially compress to a substantial degree (e.g., become reduced in length by more than about 1%) in the presence of axial force being applied thereto at one or both ends thereof consistent with the tension forces present on native chordae tendineae during normal physiological conditions in a human patient. The sutures 209 may pass through a pledget 206 and into the tube 205 of the suture-tensioning device 200, wherein the tube 205 is disposed and/or pressed against a proximal side of the pledget 206, as shown. The sutures may further pass through one or more channels internal to one or more other components of the suture-tensioning device 200, such as within a central lumen or channel of the plunger 220 and/or a central channel or lumen of a plunger translation track member or housing 210, in which the plunger 220 may be at least partially disposed during operation thereof.

With the suture(s) 209 fixed to the plunger member 220, the distance between the fixation point of the suture(s) 209 and the distal end of the tube 205 may be substantially fixed with respect to a central longitudinal axis of the device 200 and/or tube 205 extending therefrom. That is, with the tube 205 coupled to the plunger track member 210 in a fixed manner, the distance between the proximal end of the plunger track member 210 and the distal end of the tube 205 with respect to a central axis running through the plunger track member 210 and through the tube 205 is substantially fixed. Therefore, axial translation of the plunger 220 along the axis 201 relative to the plunger track member 210 may thereby change the distance between the fixation point of the suture(s) 209 with the suture fixation member 260 and the distal end 202 of the tube 205, thereby resulting in a change in the tension experienced by the suture(s) 209 distal to the fixation point of the sutures 209 (e.g., the proximal end aperture 265 of the plunger 220). Processes disclosed herein provide for suture tension adjustment through the axial translation of the plunger member 220 relative to the plunger track member 210, as described in greater detail below.

The plunger track member 210 can serve both to house at least a portion of the plunger 220 as well as to provide a structure and/or surface for manual holding of the device 200. In some examples, the plunger track member 210 as a hexagonal outer surface, as shown, or another exterior surface providing convenient services for holding, such as one or more flat surfaces, as shown. In some examples, the exterior surface of the plunger track member is at least partially curved and/or cylindrical.

With one or more suture portions 209 disposed within the device 200 and tube 205 and fixed to one or more portions of the plunger 220, the tube 205 and suture contained therein may operate in a similar manner to a cable-actuated wheel-breaking assembly, wherein separate actuators/fixtures are secured to a cable and a cable housing, respectively. For example, the tube 205 may provide a relatively stable exterior, whereas the suture(s) contained therein can operate as a moving component within the tube 205, which serves to pull on a tissue anchor or other device connected at a distal end to the suture(s).

Although examples of the present disclosure relate to plunger members configured to fix sutures at or near a proximal end of the plunger, it should be understood that suture fixation may be implemented at any axial portion of a plunger. That is, plunger members in accordance with aspects of the present disclosure may be configured to fix sutures thereto in any suitable or desirable way or at any suitable or desirable area or portion of the plunger.

In some examples, the elongate plunger member 220 comprises a screw portion 329 (see FIG. 12) having one or more screw threads associated therewith, as shown. Although certain figures are presented herewith showing plunger members having male screw threads, it should be understood that plunger members in accordance with examples of the present disclosure may alternatively have female screw threads associated therewith. The screw threads of the plunger 220 may be configured to fit within corresponding threads of a rotatable plunger actuator member 230, such that rotation of the plunger actuator 230 axially displaces/translates the plunger 220 with respect to the plunger track 210. In operation, as the plunger actuator 230 is rotated, the screw-type plunger 220 is displaced forward or backward depending on the direction of rotation of the actuator 230. Such translation will serve to either tighten or loosen the tension on the sutures 209 distal to the pledget 206 (e.g., within the target heart ventricle). The tension of the sutures 209 may generally not be tightened or loosened in response to plunger translation with respect to portions thereof that are proximal to the fixation device 260 and/or proximal end 265 of the plunger 220.

The tube 205 advantageously maintains a fixed or set distance $d_0$ between the distal end of the plunger track member 210 and the pledget 206, against which the distal end 202 of the tube 205 may be pressed or disposed during operation. Furthermore, use of the tube 205 may allow for the advancement of the device 200 (e.g., tube 205) inside the surgical cavity. For example, thoracotomy, sternotomy, small left thoracotomy, or other as procedures may be implemented, as described above, to provide access down inside the chest cavity to the ventricle wall (e.g., left ventricle wall) of the heart. With the pledget positioned against the ventricle wall, the sutures passing through the ventricle wall can be threaded through the pledget, as detailed above. Therefore, the tube 205 may allow for the creation of a relatively small incision, while still providing access down to the heart in a relatively flexible manner enable by the lateral flexibility of the tube 205. For example, the tube 25 may be bendably flexible in space but axially stable, such that the length $d_0$ of the tube 205 does not substantially change when an axial load is applied thereto. The tube may have any suitable or desirable length dimension do, such as approximately 10 inches (about 25 cm). The ability to bend and move the tube 205 and device 200 in space can provide convenience in positioning the device 200 out of the way of other surgical tools and/or to occupy a space this convenient from a surgical perspective. In some examples, the device 200 does not include a distal tube. In such examples it may be necessary or desirable to hold the distal end of the plunger track member 210 against the pledget 206 in order to maintain a fixed distance between the suture-locking feature 260 and the pledget 206. However, the use of the tube 205 can allow for offsetting of distance between the device 200 and the pledget 206, thereby providing greater convenience. The tube 205 may have any suitable or desirable material, such as transparent plastic having a wall thickness that is sufficient to provide the necessary or desirable axial stability.

The suture-locking feature 260 associated with the plunger 220 may be any suitable or desirable suture-fixation feature. In some examples, the locking feature 260 can be used as a temporary lock, wherein no knot-tying is required to fix or lock sutures thereto. For example, in some examples, the sutures 209 may be pulled through the proximal end 265 of the plunger 220, wrapped around a base 269 of the locking feature 260, and drawn through a slot 262 or other feature configured to provide for a friction hold of the sutures 209 therein. Such wrapping may reduce the risk of unraveling of the suture(s) 209. Prior to fixation/locking of the sutures 209 to the suture-locking feature 260, the device 200 may effectively float along the length of the sutures, such that the device may slide along the length of the sutures, which allows for the device to be advanced to abut the pledget 206, as shown in FIG. 11.

Figure 12:
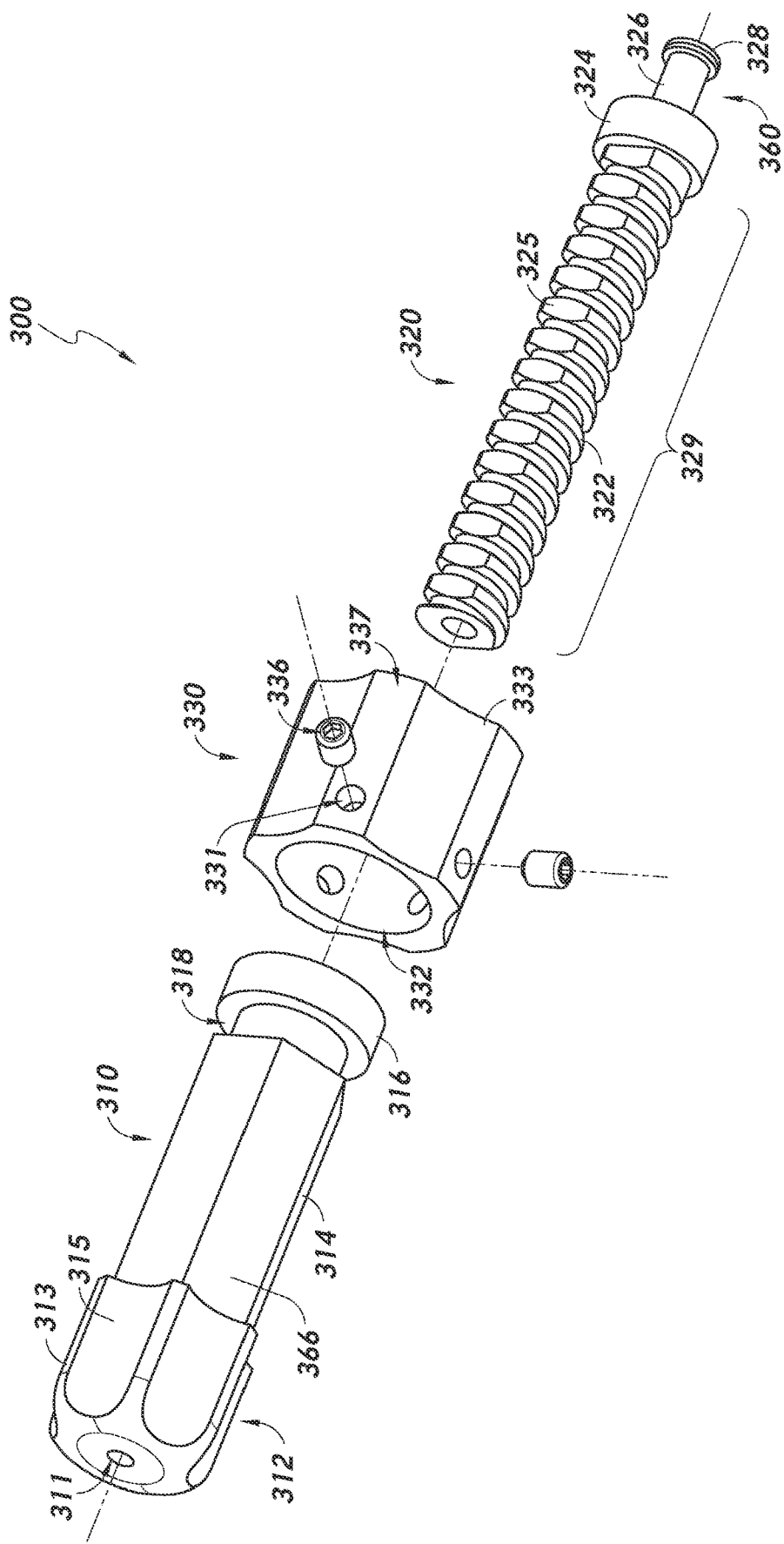
FIG. 12 shows an exploded view of a suture-tensioning device in accordance with one or more examples.
Figure 17:
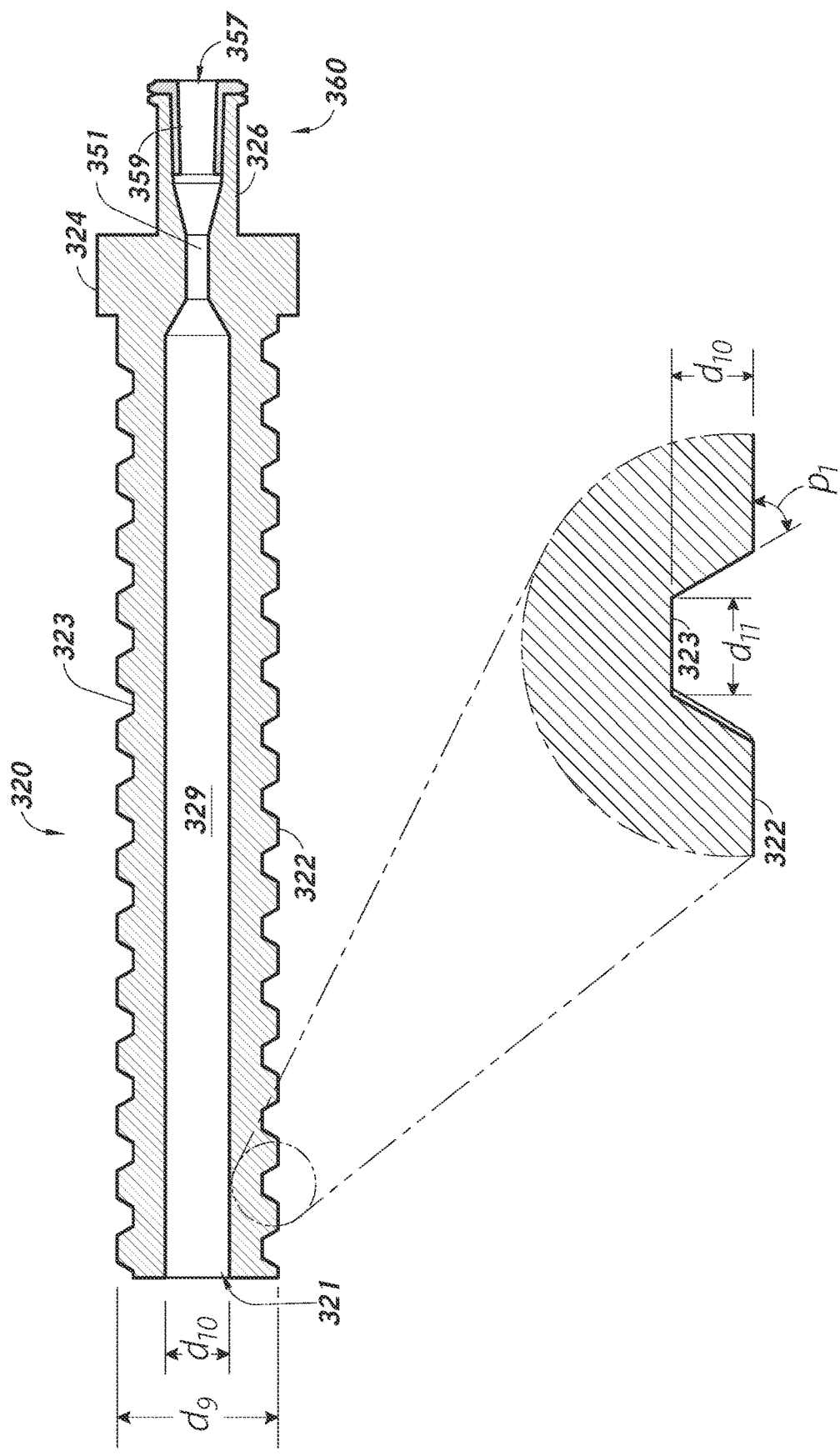
FIG. 17 shows a cross-sectional view of the plunger member shown in FIG. 15 in accordance with one or more examples.
Figure 19:
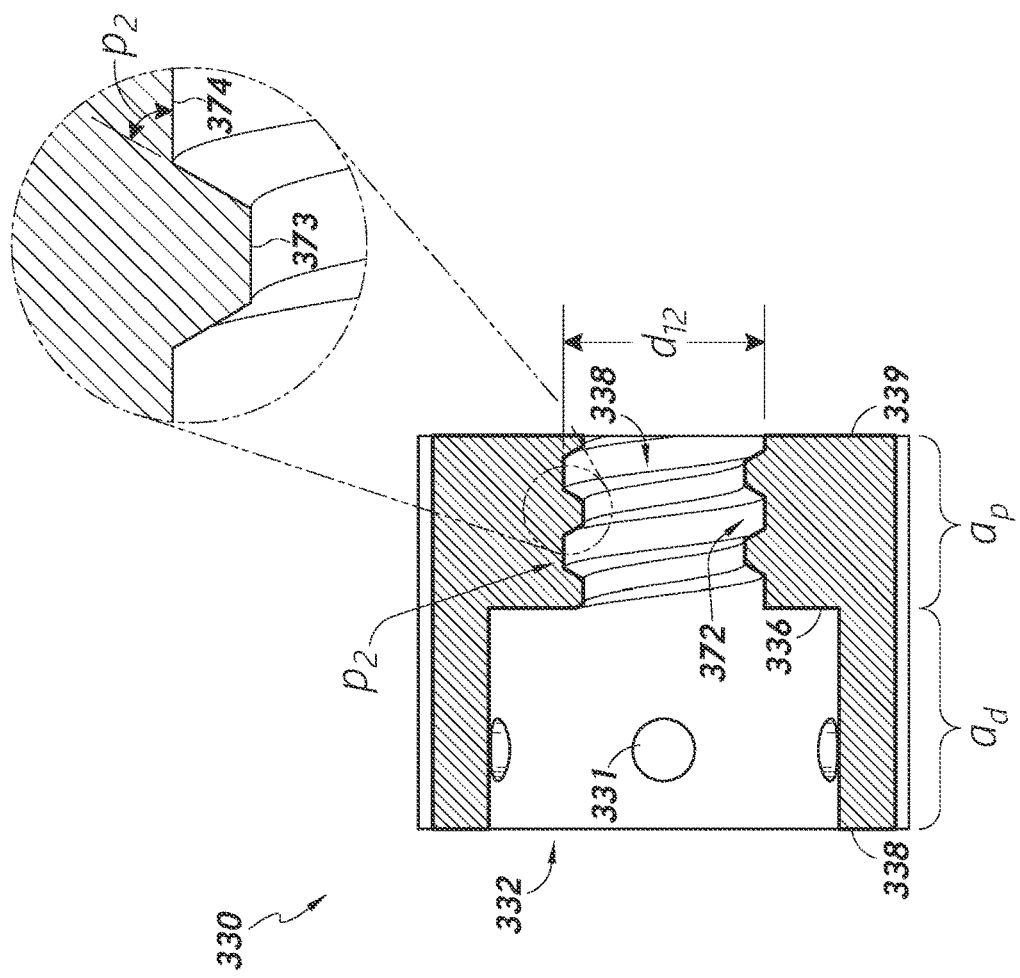
FIG. 19 shows a cross-sectional side view of the plunger actuator shown in FIG. 18 in accordance with one or more examples.
Figure 18:
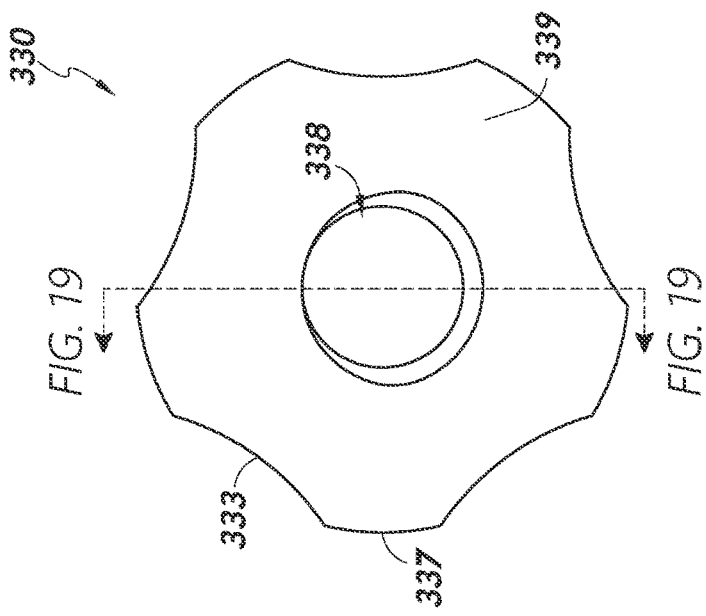
FIG. 18 shows a proximal end view of a plunger actuator of the suture-tensioning device shown in FIG. 12 in accordance with one or more examples.

The following description relates to FIGS. 12-19, which illustrate certain views of various components of a suture-tensioning device 300. Specifically, FIG. 12 shows an exploded view of the suture-tensioning device 300 in accordance with one or more examples. FIG. 13 shows a cross-sectional side view of a plunger track member 310 of the suture-tensioning device 300 in accordance with one or more examples. FIG. 14 shows a proximal end view of the plunger track member 310 shown in FIG. 13 in accordance with one or more examples. FIG. 15 shows a side view of a plunger member 320 of the suture-tensioning device 300 in accordance with one or more examples. FIG. 16 shows a distal end view of the plunger member 320 shown in FIG. 15 in accordance with one or more examples. FIG. 17 shows a cross-sectional view of the plunger member 320 shown in FIG. 15 in accordance with one or more examples. FIG. 18 shows a proximal end view of a plunger actuator 330 of the suture-tensioning device 300 in accordance with one or more examples. FIG. 19 shows a cross-sectional side view of the plunger actuator 330 shown in FIG. 18 in accordance with one or more examples. The suture-tensioning device 300 may represent an example of the suture-tensioning device 200 shown in FIG. 11. Therefore, the following description is relevant to the examples described above with respect to FIG. 11.

With reference to FIG. 13, the plunger track member 310 can provide a tourniquet-type tube in which sutures and portion of the plunger 320 can be contained. The plunger track member 310 includes a hole/opening forming a channel/cavity 311 that provide access to the primary internal channel 319 (e.g., the plunger track) of the plunger track member 310. The relatively small hole/opening to the channel/cavity 311 further provides access from the plunger track member 310 to an axially-rigid suture-tensioning tube 305 when the tube 305 is inserted therein. The tube-fit channel/opening 311 can receive therein the proximal end of the tube 305. The plunger track member 310 may have any suitable or desirable length $d_1$, such as approximately 3 inches (about 75 mm).

The tube component 305 (e.g., similar to the tube member 205 of FIG. 11) may be disposed at least partially within the distal end 312 of the plunger track member 310. However, the tube 305 may generally not traverse the length $d_1$ of the plunger track member 310. The tube 305 may be disposed within a cavity, opening, channel, and/or other feature 311 accessible from the proximal end of the plunger track 310. The cavity/channel 311 may occupy only an axial portion of the member 310, which may be referred to as a tube-fit portion 391. The tube fit portion 391 of the plunger track 310 may end at a relatively narrow channel 341, wherein the interface between the wider tube-fit channel 311 and the narrow channel 341 may provide a seating surface against which the tube 305 and/or adhesive or other attachment means may be disposed and/or placed. The tube-fit channel 311 may have any suitable or desirable diameter $d_3$, such as approximately 0.125 inches (about 3 mm).

Although the tube 305 advantageously does not axially compress, the tube 305 may be flexible, thereby allowing for manipulation of the position of the device 300 while still maintaining the fixed distance between the distal end of the device 300 and the distal end of the tube 305.

The actuator 330 is configured to be rotatably secured to/over the proximal end of the plunger track housing 310. For example, the proximal end of the plunger track housing 310 can include the flange 316 and/or one or more other portions/features of the housing 310. With reference to FIGS. 12, 18, and 19, as the plunger actuator 330 is rotated, the plunger 320 is actually translated, as described above. However, the plunger 320 and/or plunger track member 310 may advantageously be configured to prevent and/or restrain the plunger 320 from rotating, such as might otherwise occur to some degree when the plunger actuator 330 rotates. Such features may be beneficial to prevent twisting of the sutures 309. Furthermore, rotation of the plunger 320 might at least partially defeat the axial translation functionality of the device 300. For example, if the plunger 320 is permitted to rotate together with the plunger actuator 330, such as due to frictional force between corresponding threads of the plunger 320 and the actuator 330, the pitch of the threads may not cause adequate forward or backward relative movement/translation of the plunger 320, which is generally effected by the relative movement of the threads of the plunger 320 with respect to the corresponding threads of the plunger actuator 330. In order to impede rotation of the plunger 320, in some examples, the threads and/or outer surface of the screw portion of the plunger may be flattened or cut-off to reduce the radius thereof along one or more sides of the plunger 320. Such reduced radius may still be permitted to slide along the internal threads of the actuator 330, while providing an axial cross-sectional shape of the threaded portion of the plunger 320 that does not have continuous/circular symmetry. Therefore, when the receiving conduit or channel 319 of the plunger track member 310 that is open from a proximal end thereof has a shape that corresponds to the axial cross-section of the plunger 320, such mating of the plunger 320 within the plunger track member 310 may serve to at least partially restrain rotation of the plunger 320 therein. Therefore, rotation of the actuator 330 may translate substantially entirely to axial translation, rather than rotation, of the plunger 320. The plunger 320 may be considered an elongate structure/plunger in that it has an axial length dimension that is greater than its width/diameter, as shown.

In some examples, the plunger 320 and/or other component(s) of the suture-tensioning device 300 has associated therewith one or more loadcell devices, or other type of force transducer(s), configured to provide/generate electrical signals indicative of an amount of force or pressure on one or more portions of the plunger 320 as a result of locking the tension sutures 309 thereto. For example, the loadcell may be configured to measure the tension on a specific suture or pair of sutures to provide information indicating whether or not the suture(s) is/are over- or under-tensioned. In some examples, the loadcell is substantially independent of the plunger 320. In some examples, piezoelectric loadcell(s) is/are implemented. For examples incorporating one or more loadcells, once the sutures are locked thereto, the compression caused by the tension pull of the sutures on the suture-locking feature may provide a relative load compared to one or more other components of the suture-tensioning device, such as the plunger actuator 330, plunger track member 310, and/or screw portion 329 of the plunger 320.

In some examples, the load presented by the tension of the sutures may be monitored in combination with one or more other mechanisms/processes for judging tension, such as imaging. In some examples, the registered load of the loadcell(s) process to account for cyclical pressure conditions attributable to the beating of the heart. Generally, the reading of the loadcell(s) indicates the maximum load on the sutures throughout the cardiac cycle. In some examples, a loadcell may be used that includes a window allowing or visible indication of relative load, such as by using relative load markings or the like. In examples disclosed herein including loadcell(s) incorporated with suture-tensioning plunger components or other component(s) of a suture-tensioning device, the loadcell or other force-gauge device may indicate the force applied on the sutures during the tensioning process, and/or ultimately the final tension on sutures at the end of the pension process. Furthermore, force/tension readings can be performed using any type of load cell, force gauge, or mechanical gauge, such as a compression screw, which may correlate the amount of movement in a spring or other device to a force value.

With reference to FIGS. 12, 18, and 19, the plunger actuator 330 is configured to be rotated to drive the plunger 320 in an axial direction to effect a change in length of suture portion(s) that are contained within the suture-tensioning device 300. The plunger actuator 330 may be configured with one or more features designed to secure the actuator 330 to the proximal end portion of the plunger track housing 310 in such a manner as to allow for rotational freedom of the actuator 330 about the plunger track member 310, while restraining axial relative movement between the actuator 330 and the plunger track member 310. Such functionality may be accomplished using a circumferential trench or channel 318 of the plunger track member 310 into which one or more components of the plunger actuator 330 may be received, wherein the channel 318 runs circumferentially around at least a portion of the plunger track member 310 to allow for circumferential rotation of the actuator 330. For example, in some examples, one or more setscrews 336 that may be driven radially through apertures 331, such as threaded apertures, of the actuator 330 such that they project inward passed an inner cylindrical surface 332 of the actuator 330. Therefore, as one assembly step for assembling the suture-tensioning device 300, the plunger actuator 330 may be coaxially advanced over the proximal end portion or flange 316, wherein the setscrews 336 may be driven radially inward into the channel 318 to axially secure the actuator 330 to the plunger track member 310. As shown, the circumferential channel 318 may advantageously be radially-open to allow for inward radial projection into the channel 318 by one or more axial locking/securing features associated with the plunger actuator 330 (e.g., setscrew(s), clip(s), ridge(s), or the like). The channel 318 may have any suitable or desirable width $d_2$, such as approximately 0.125 inches (about 3 mm).

It may be desirable for the setscrews 336 to be driven radially inward to a degree to restrain axial movement of the actuator, while not locking the actuator 330 in place rotationally, such that the actuator 330 can rotate substantially freely, or with some rotational resistance. In some examples, the actuator 330 includes set screw radial advancement control/stop features to facilitate the appropriate position of the setscrews 336 within the groove/channel 318. Although setscrews are illustrated in FIG. 12 and described herein, it should be understood that the plunger actuator 330 may be secured to the plunger track member 310 in any suitable or desirable way, such as through the use of one or more clips, snap features, or other features that are configured to project radially inward past the internal cylindrical surface 332 of the actuator 330.

The suture-locking feature 360 may be any suitable or desirable feature configured to fix or secure in place one or more suture portions and prevents axial movement thereof. In some examples, the suture-locking feature 360 includes one or more pegs 326, plugs 359, and/or other features that may be employed to wrap and/or otherwise secure suture portions thereto. For example, in some examples, the suture-locking feature 360 comprises a stopcock feature, which may include a valve-type assembly. For example, a rotatable handle or other actuator feature may be rotated to lock sutures passing therethrough in place against an inner surface of the peg component 326. In some examples, the suture-locking feature 360 is a Luer-type feature, wherein the peg feature 326 includes a relatively wide-diameter channel 357, which may be tapered, and a plug component 359 may be inserted and/or pressed therein to lock suture portions between the plug 359 and the outer cylinder 326. FIGS. 16 and 17 show the suture-fixation feature 360 as a Luer assembly, including the hollow peg 326 and the plug 359 dimensioned to fit at least partially within the peg 326.

The plunger track housing 310 includes an internal plunger track/channel 319. The plunger track 319 in dimensioned to receive, in the direction of length of the housing 310 (e.g., the distal direction), some or all of the screw portion 329 of the plunger component/member 320. For example, the plunger 320 can be inserted into the plunger track 319 via the non-circular, proximally-facing opening 317. The axial opening 317, as shown, can have a truncated circle or oval/ellipse shape in the axial perspective, as shown in FIG. 14, which is advantageously dimensioned/configured to receive the plunger therein and restrict axial rotation of the plunger 320. The screw portion 329 of the plunger 320 can fit inside the plunger track 319 in such a way as to allow the plunger actuator 330 to drive the plunger forward and backward, while preventing the plunger 320 from rotating. For example, the actuator 330 may be configured to be actuated to cause axial translation of at least a portion of the plunger 320 within the plunger track 319, as described in detail herein in connection with various examples.

The plunger 320, or at least a threaded portion 329 thereof, may have an oblong-type cross-sectional shape to match a corresponding shape of the opening 317 in the proximal end of the plunger track housing 310 (see FIG. 14). For example, in some examples, the cross-sectional shape of the plunger track 319 and the threaded portion 329 of the plunger 320 is a circle with one or more sides cut or formed to produce one or more substantially flat sides. In some examples, the flat sides are formed on opposite sides of the axial cross-section of the plunger (see FIG. 16), which are matched by the corresponding receiving track 319 of the plunger track housing 310. The distance between the flat sides 325 of the screw portion 329 of the plunger 320 may be any suitable or desirable distance $d_4$, such as approximately 0.25 inches (about 6 mm).

The plunger 320, as shown in the cross-sectional view of FIG. 17, includes an internal conduit or channel 329 through which suture portions may traverse the plunger 320 via the channel 351, which may be relatively narrow, and/or the channel formed by the peg/cylinder 326. The threaded portion 329 of the plunger may have any suitable or desirable length. Generally, the length $d_5$ of the threaded portion 329 of the plunger 320 may determine the tuning range of the suture-tensioning device 300. In examples including a narrow internal channel 351 in the plunger 320, such narrowing of channel may serve to facilitate the advancement of a snare wire through the suture-tensioning device. The screw portion 329 of the plunger 320 may have any suitable or desirable length $d_5$, such as approximately 4 inches (about 10 cm).

In some examples, the plunger 320 comprises a proximal flange 324, which may serve to limit the axial movement of the plunger 320. For example, the flange 324 may prevent translation of the plunger 320 into the plunger actuator 330 beyond the distal surface of the flange 324. The flange 324 may have any suitable or desirable thickness $d_6$ and/or diameter $d_7$, such as approximately 0.125 and 0.375 inches (about 3 and 10 mm), respectively.

In some examples, the proximal portion 328 of the plunger 320 may have associated therewith a tension loadcell component configured to measure the tension on the sutures passing through the internal channel 329. For example, the plunger 320 may comprise a loadcell positioned between the threaded portion 329 of plunger 320 and the suture-fixation feature/component 360. Such a loadcell may advantageously be sensitive to relatively low loads, as may be expected on sutures in a heart valve repair procedure. Such loadcell(s) may be a piezoelectric loadcell(s), for example, wherein application or release of load across the loadcell results in changes to impedance characteristics thereof. In some examples, the flange 324 comprises plates or cylinders having piezoelectric material disposed therebetween, wherein a voltage difference between the plates provides a relative force/tension measurement. In some examples, the loadcell feature is configured to measure tensile forces or pressure, such that tension on sutures fixed directly or indirectly thereto creates a compressive load across the loadcell indicative of suture tension. Where the flange 324 incorporates a loadcell feature, one side of the loadcell may be mechanically coupled to and/or associated with the threaded portion 329, while the other side of the loadcell may be mechanically coupled to and/or associated with the suture-fixation feature 360. Wires associated with the loadcell(s) may advantageously be disposed such that they do not exhibit any force on the loadcell that would change or affect the force reading. Rather, loadcell wiring may be configured to project from the diameter of the loadcell, such that the wires essentially float with respect to the tension on the sutures.

The radially-projecting screw threads 322 (flatten portions thereof shown in FIG. 17) may have a relatively smaller-diameter portion 323 separating axially-adjacent thread portions. Although the examples of FIGS. 15 and 16 show threads 322 that are radially flattened over two circumferential segments (specifically, two opposite circumferential segments), it should be understood that plunger components/devices in accordance with the present disclosure may have any suitable or desirable number and/or width or radius dimension of radially-flattened segment(s). The treaded portion 329 of the plunger 320 may have threads with any suitable or desirable pitch $p_1$, thread-to-thread spacing $d_{11}$, and/or thread height $d_{10}$, such as approximately 0.2, 0.06, and 0.05 inches (about 5, 1.5, and 1.25 mm), respectively.

In some examples, suture-tensioning devices in accordance with the present disclosure include loadcell features associated with the interface between the tube component and the suture track housing component. Alternatively or additionally, load cell features may be integrated with the distal end of the tube where tube presses against the pledget. However, such solutions may suffer from certain losses with respect to translation of tension forces from the sutures, and therefore may not be as precise as solutions incorporating loadcell features with the plunger member at or near the point of the fixation of the sutures with the plunger.

The plunger actuator 330, shown in cross-sectional view in FIG. 19, includes a threaded area $a_p$ and a coupling area $a_d$. Generally, the threaded area $a_p$ may be at, and/or associated with, a proximal side of the actuator 330, which is shown in FIG. 18, whereas the coupling area $a_d$ may be at, and/or associated with, a distal side of the actuator 330. The axial length of the threaded portion $a_p$ may be any suitable or desirable length. Generally, it may be desirable for the length of the threaded portion $a_p$ to be sufficient to include enough turns of threads to be securely coupled with the corresponding threaded portion 329 of the plunger member 320. An internal axial rim 336 between the coupling area as and the threaded area $a_p$ may provide a seating against which the proximal end surface 313 of the plunger track member 310 may be stopped when the plunger actuator 330 is placed over the proximal end of the plunger track member 310 and coupled thereto (e.g., using setscrews projecting through radial apertures 331). Examples of the present disclosure may include other types of coupling features in addition to, or in alternative to, the setscrews (not shown in FIG. 19) and screw apertures 331, such as certain ridge or clip features configured to occupy some of the radial space within a corresponding open circumferential groove/channel 318 of the plunger track housing 310. The radially-oriented threaded apertures 331 can be configured to have any type of setscrew(s) or other type of feature(s) engaged therewith that can be disposed/driven in such a manner as to penetrate an internal cylindrical plane associated with the internal cylindrical surface of the coupling area $a_d$.

The plunger actuator 330 includes internal threads 372 that are configured to mate with the threads of the screw portion 329 of the plunger 320. For example, as shown, the threads 372 can project radially inward and/or have thread recesses that project into the structure of the threaded portion $a_p$ of the actuator 330 (e.g., radially outward). In some examples, the threads 372 may be considered female threads, while the threads 322 of the plunger 320 can be considered male threads. The treaded portion of the actuator 330 may have threads with any suitable or desirable pitch $p_2$, such as approximately 60°, wherein such pitch may be similar to the pitch $p_1$ of the plunger threads 322.

Tensioning Processes

Figures 1, 21:
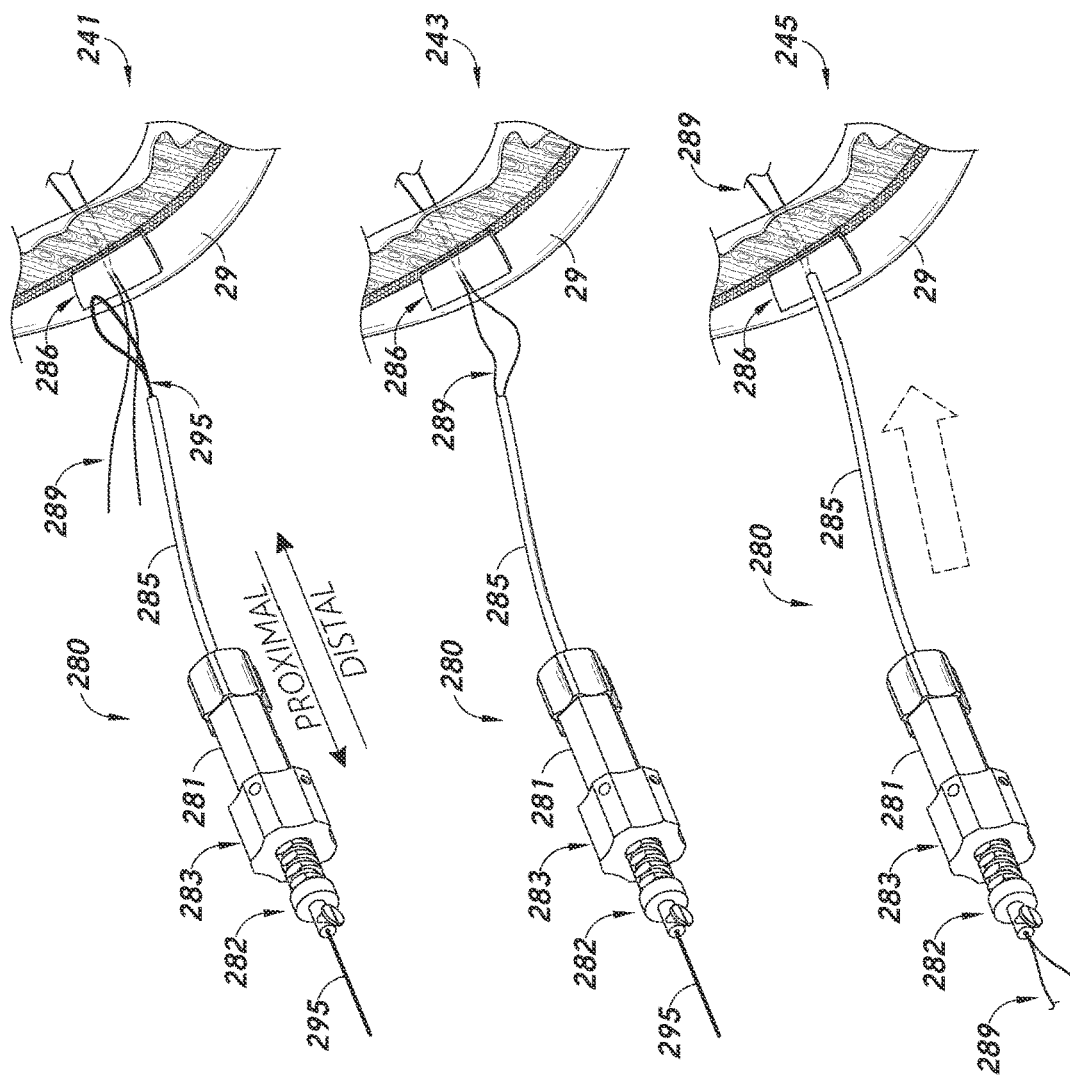
Figures 1, 20:
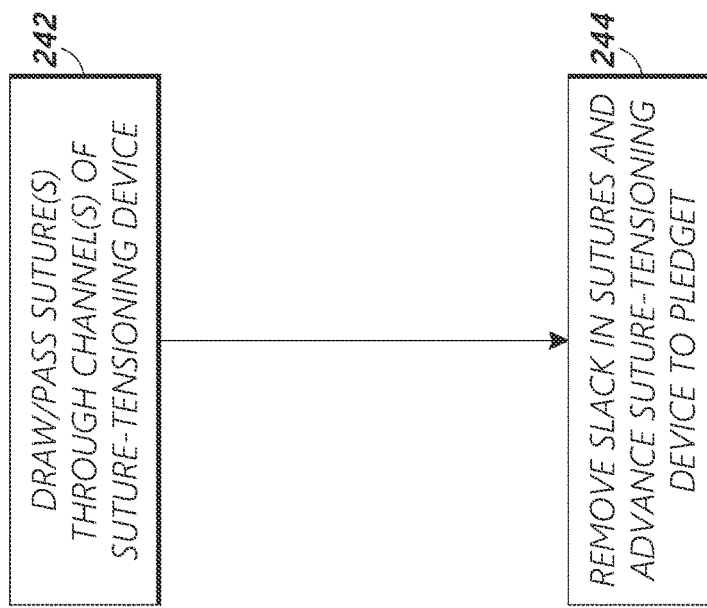
Figures 2, 21:
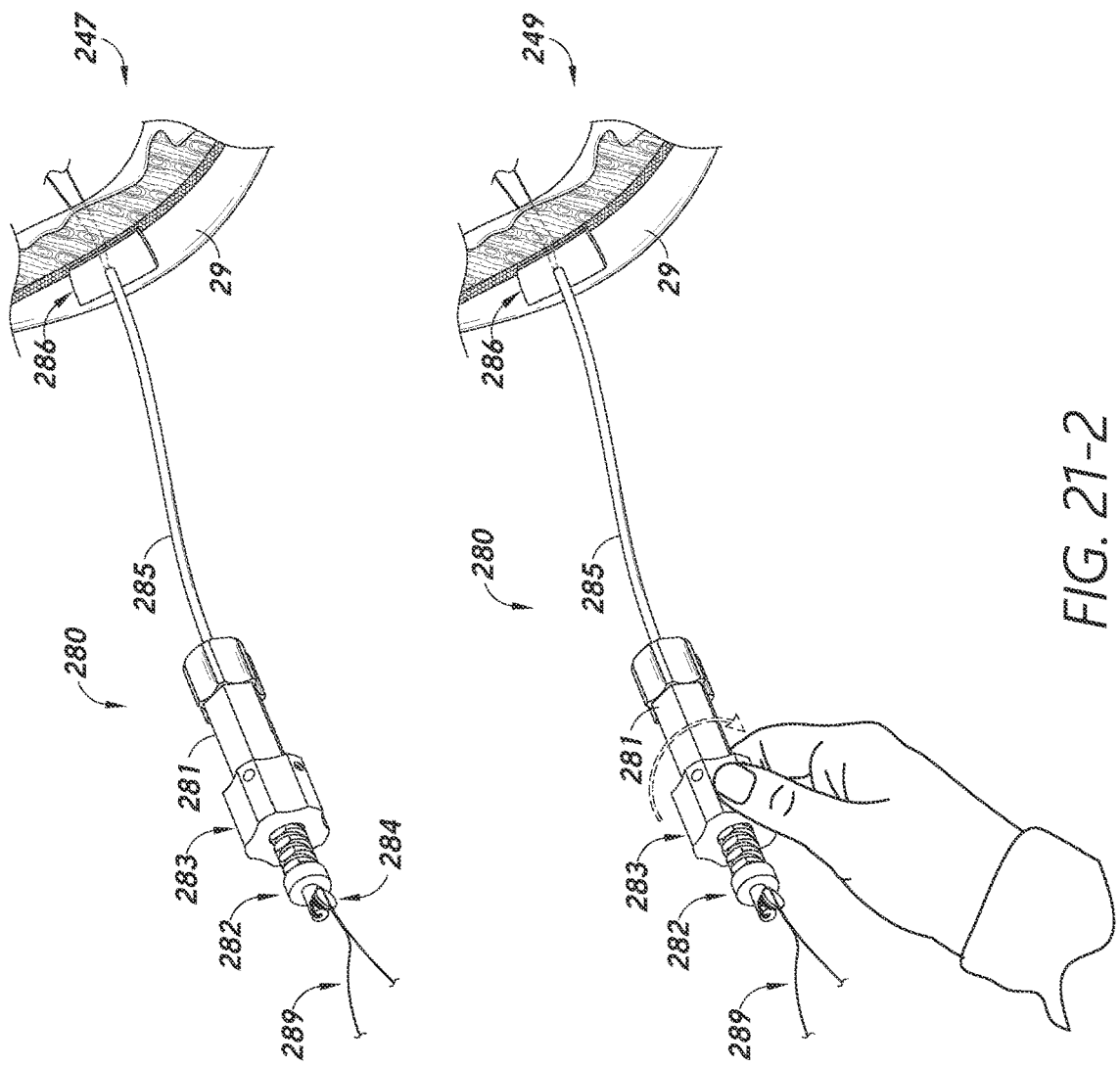
Figures 2, 20:
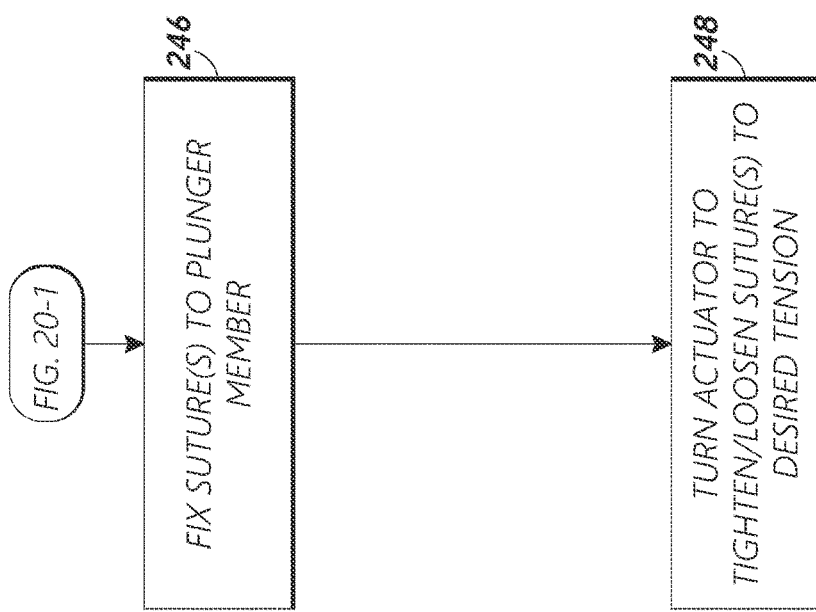
Figures 3, 21:
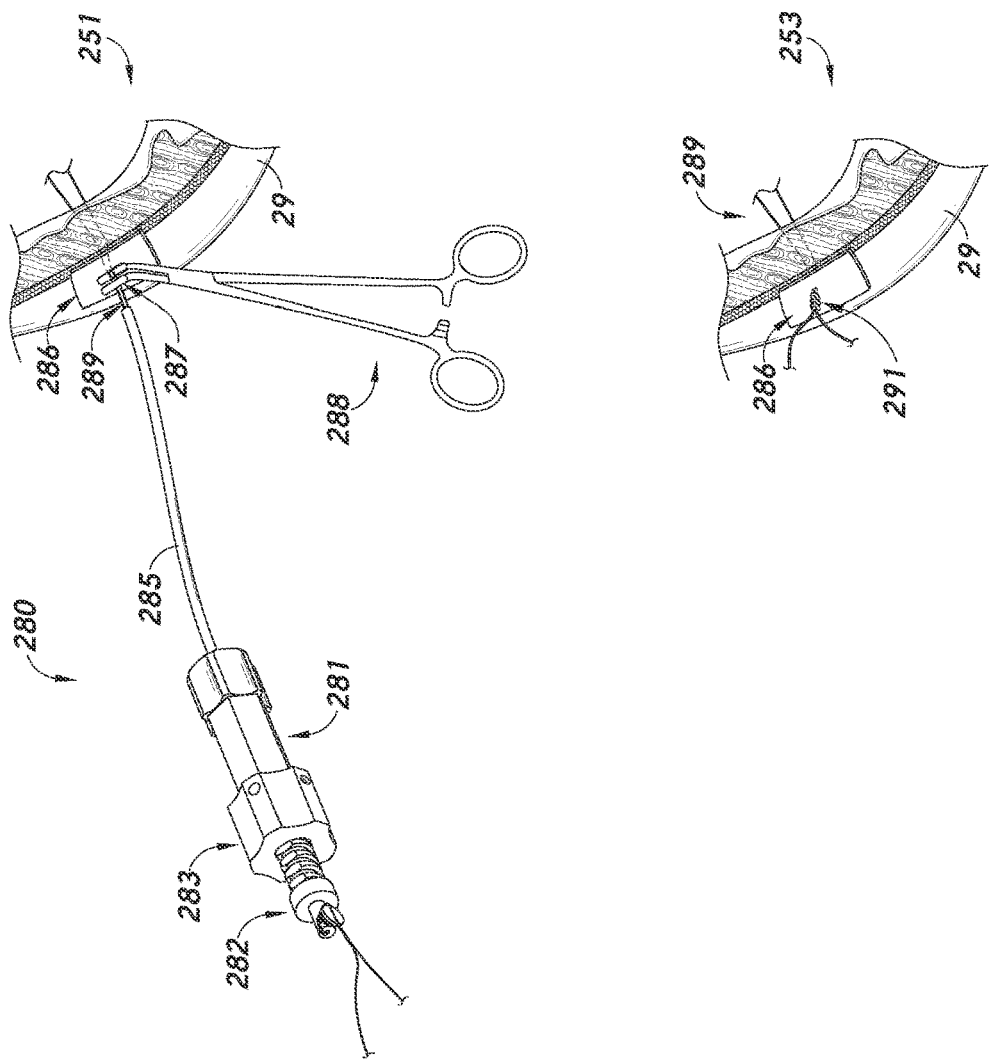
Figures 3, 20:
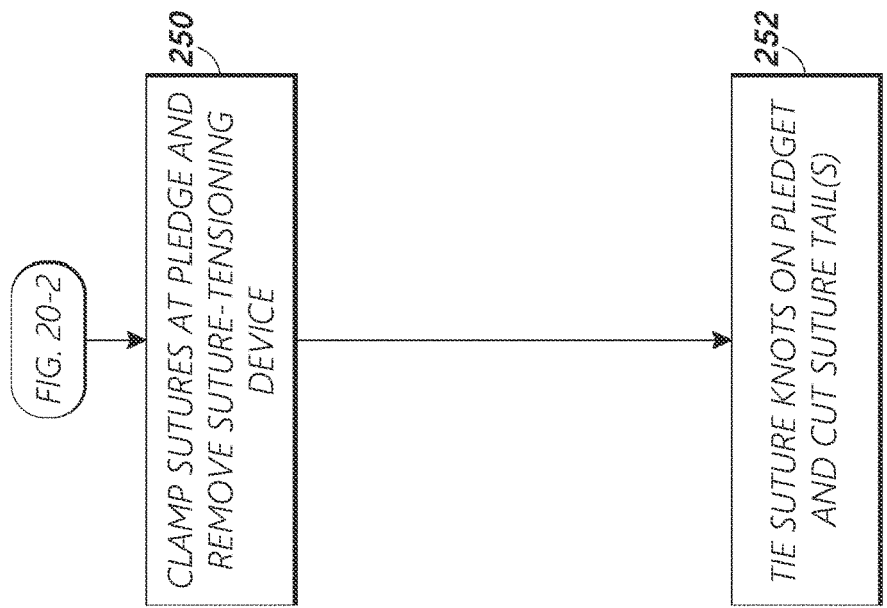

The various examples of suture-tensioning devices disclosed herein may be used in any suitable or desirable way or manner. FIGS. 20-1, 20-2, and 20-3 (collectively referred to as FIG. 20) provide a flow diagram illustrating an example process 240 for tensioning sutures in accordance with one or more examples. FIGS. 21-1, 21-2, and 21-3 (collectively referred to as FIG. 21) show certain images corresponding to respective blocks, states, and/or operations associated with the process 240 of FIG. 20 in accordance with one or more examples. The images of FIG. 21 are provide for reference. However, it should be understood that any of the illustrated and/or disclosed example presented herewith may be used and/or relevant to the various operations associated with the various block of the process 240 of FIG. 20.

The process 240 may be implemented to tension a single suture or suture pair, such as a pair of suture tails coupled to, and/or otherwise associated with, a single tissue anchor (e.g., bulky knot heart valve leaflet anchor). Alternatively, the process 240 may be implemented to tension a plurality of suture pairs, or a plurality of sutures associated with separate respective tissue anchors, simultaneously. Simultaneous tensioning of a plurality of sutures or suture pairs can be implemented to promote/facilitate the substantially equal tensioning of such multiple sutures/suture pairs. Furthermore, it should be understood that the process 240 may be implemented to tension sutures or other devices not connected to tissue anchor implantation (e.g., non-biological/medical applications).

For sequential tensioning of multiple pairs of sutures, the process 240 may be repeated, at least in part, a plurality of times to place and/or tension a plurality of suture pairs associated with a plurality of respective tissue anchors. For example, the process 240 may be implemented to place between two and six pairs of sutures, each pair being associated with a separate tissue anchor (e.g., knot-type tissue anchor).

The process 240 may be preceded by the pulling, threading, and/or otherwise drawing the pair(s) of sutures 289 (e.g., pair-by-pair) through a pledget, such as a pledget ultimately placed against the exterior wall 29 of a heart or other biological tissue in connection with a medical procedure. When the suture pair(s) 289 is/are pulled/drawn through the pledget 286, the pledget may not be tied-down or otherwise secured to biological tissue 29 (e.g., ventricle wall) other than through the frictional force of the sutures passing therethrough. The process 240 may involve sliding the pledget down the sutures until appropriate contact is made with the ventricle wall. The operations relating to passing the suture(s)/suture pair(s) 289 through the pledget 286 may or may not be considered part of the process 240.

At block 242, the process 240 involves drawing or otherwise loading the one or more sutures 289 (e.g., a suture pair) into/through channel(s) of a suture-tensioning device 280. For example, such channels may include one or more internal channels associated with one or more of a plunger component 282 and a plunger track component 281 of the suture-tensioning device 280, as described in detail herein. In order to load the suture(s) 289 into the device 280, a snare wire 295 or similar device may be used pulled the ends of the sutures 289 (e.g., suture tails coupled to a tissue anchor) through the suture-tensioning device 280.

The suture(s) 289 may be pulled or otherwise placed in/through the various channels/conduits of the suture-tensioning device 280 in any suitable or desirable manner. For example, as referenced above, a snare wire 295 associated with, e.g., a suture snare wire puller device 295, may be advanced through the suture-tensioning device 280, as well as through a distal suture tubing component 285 associated therewith. Generally, the snare wire 295 may form a loop at or near a distal end thereof, which may protrude from the distal end of the tubing 285 of the suture-tensioning device 280.

The process 240 may involve threading ends of the particular suture(s)/suture pair(s) 289 through the loop of the snare wire 295 and pulling the snare wire 295 back through the suture-tensioning device 280 to draw the suture(s) 289 through the channels/conduits of the suture-tensioning device 280. In some examples, the snare wire puller device with which the snare wire 295 is associated may comprise a proximal handle, which may be used to advance the snare wire 295 through the suture-tensioning device 280 and/or to pull/draw the captured sutures back through the suture-tensioning device 280 in the proximal direction.

The snare wire 295 may be any suitable or desirable type of snare wire, and may have a thickness of, as an example, approximately 0.006 inches (about 150 μm). The snare wire 295 can comprise Nitinol or any other material. The snare wire 295 may advantageously be sufficiently stiff to create interference with the inner diameters of the tubing 285 and other component(s) of the suture-tensioning device 280 as the snare wire is pulled therethrough with the captured suture(s) 289. In some examples, the snare wire 295 may be pre-disposed within the suture-tensioning device 280 at the outset of the process 240, such that the surgeon/technician need not advance the snare wire through the device. The image 241 of FIG. 21-1 shows the suture-tensioning device 280 with the snare wire 295 disposed therein.

After pulling the suture(s) 289 through the suture-tensioning device in connection with block 242, the suture(s) 289 may be disposed as shown in image 243 of FIG. 21-1. As shown in image 243, some amount of slack may be present in the suture(s) 289 distal to the tube 285 and/or within the tube 285/device 280. At block 244, the process 240 involves removing the slack in the suture(s) 289 and advancing the suture-tensioning device 280 (e.g., the distal end of the tube 285) to the pledget 286. For example, the process 240 may involve pulling the suture(s) 289 in the proximal direction in order to reduce or eliminate slack in the sutures, both within the suture-tensioning device 280 and distal to the tubing 285 and/or pledget 286 (e.g., within the ventricle of the heart of the patient). Image 245 of FIG. 21-1 shows the tube 285 disposed against the pledget 286.

At block 246, the process 240 involves fixing the suture(s) 289 to one or more portions of the plunger component 282 of the suture-tensioning device 280. Fixing the suture(s) 289 to the plunger component 282 may involve engaging a portion of the suture(s) 289 with a suture fixation/locking mechanism 284 associated with a proximal end portion of the plunger component 282 of the suture-tensioning device 280. For example, fixing/locking the suture(s) 289 may involve wrapping the suture(s) 289 around one or more structures or features of the suture fixation/locking mechanism 284 to create frictional fixation of the sutures to the plunger component 282. In some examples, the suture fixation/locking mechanism 284 comprises a screwhead-type form with a slot formed therein, wherein the sutures may be wrapped around a base of the screwhead form and into the slot, the slot being sized to hold the sutures therein. Image 247 shows the suture 289 wrapped around the suture-fixation feature 284 of the plunger component 282.

At block 248, the process 240 involves turning/rotating or otherwise manipulating an actuator component 283 of the suture-tensioning device 280, which may be coupled to both the plunger 282 and the plunger track 281, to tighten and/or loosen the suture(s) 289 distal to the suture-fixation feature 284 to a desired tension level. The actuator 283 may be configured to, when manipulated/rotated, adjust a relative axial position between the plunger component 282 and the plunger track component 281 to adjust the tension of at least a portion of the suture(s) 289. Adjusting the tension in the suture(s) 289 may increase the length dimension between the suture-fixation point/feature 284 of the plunger component 282, or to a proximal end of the plunger member through which the sutures are drawn prior to fixation thereof, and the distal end of the tube component 285. Such adjustment(s) may be performed at least in part by rotating the actuator 283 (e.g., clockwise to tighten, counterclockwise to loosen), which is rotationally coupled to the plunger track component 281 of the suture-tensioning device 280 and is further engaged with male or female threads of the plunger member 282, as described in detail herein. Rotating the actuator 283 can drive the threads of the plunger 282 using the corresponding threads of the actuator 283 Image 249 shows actuation of the actuator component 293, as described.

While adjusting the tension of the sutures using the plunger actuator 283, the process 240 may involve simultaneously and/or intermittently monitoring leaflet movements, tissue anchor position, and/or other aspects of the patient's biology and/or implants in the patient using a suitable imaging modality, such as echo imaging. In some implementations, the use of the suture-tensioning device 280 can allow for the surgeon or technician to have the flexibility to manually release the device 280 and/or suture(s) 289 while determining the target location and/or tension for the tissue anchor implant(s) associated therewith, such as in collaboration with echocardiography or other imaging modality.

In some implementations, in connection with the operations associated with block 248, a tissue anchor implant may be assessed under hypertension conditions to determine how the implant is affected by relatively higher-pressure conditions compared to pressures under anesthesia. In such procedures, the suture-tensioning device 280 may be used to tension sutures to the desired tension, at which point pressure may be increased to assess the effect on the implants in such pressure/tension conditions.

At block 250, with the desired tension in the suture(s) 289 having been achieved, the process 240 involves clamping the suture(s) 289 at or near the pledget 286, after which the suture-tensioning device 280 may be removed from the suture(s) 289. For example, the suture(s) 289 may be clamped using rubber shoes 287, or the like, clamped between the distal end of the tube 285 and the pledget 286. Clamping the suture(s) 289 at or near the pledget 286 can serve to fix the present tension in the suture(s), due to the clamp being pulled and held against the pledget 286, as shown in image 251 of FIG. 21-3. In some implementations, clamping the suture(s) 289 involves pushing in the distal direction against the pledget 286 with the clamp 288 to displace the pledget 286 from the distal end of the tubing 285 of the suture-tensioning device 280 far enough to accommodate the rubber shoes 287 (e.g., rubber shoes on a right-angle clamp device 288) or other clamp features between the distal end of the tubing 285 and the pledget 286.

In some examples, a straight clamp (not shown) may further be clamped on the tubing 285 in order to provide further securing of the sutures thereto. However, the stiffness of the tubing 285 (e.g., plastic tubing) may make it difficult to effectively clamp the sutures through the tubing wall.

At block 252, the process 240 involves tying suture knots 291 on the pledget 286 to secure the suture tension, and cutting the excess portions of the suture tail(s). After (or before) the tying of knot(s) 291, or other fastening of the sutures (e.g., using clip(s), pin(s), or other fastening device(s)), the clamp device(s) 288 may be released. For example, releasing the clamp 288 may allow the suture knot(s) 291 (e.g., knot stack) to hold against the pledget 286. Image 253 shows a suture knot stack securing the tension of the suture(s) 289. It may be desirable to execute slight over-tensioning of the suture(s) 289 when clamping the suture(s) in place, such that when the clamp 288 is withdrawn with the knot(s) 291 tied on top of the clamp, the distance between the tissue anchors and the knots 291 is a similar distance to the distance determined or arrived at through tensioning in accordance with the process 240.

Multiple-Channel Suture-Tensioning Devices and Processes

In some implementations, the present disclosure relates to systems, devices, and methods for separately tensioning multiple sutures or pair of sutures using a single device or a cassette configured to simultaneously hold and/or secure multiple separate suture-tensioning devices. Such device(s) can further simplify suture tensioning in multiple-implant procedures.

Figure 22:
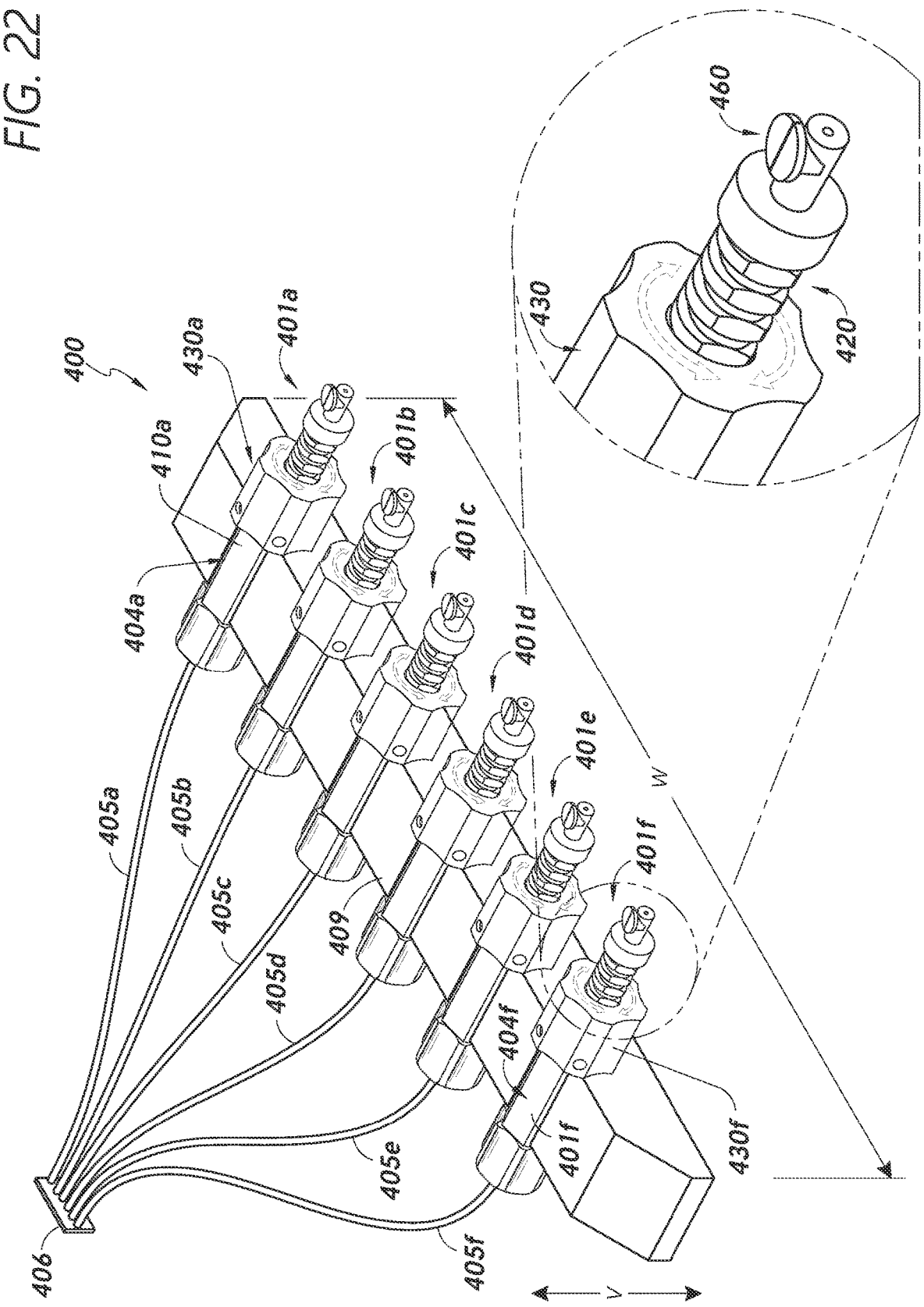
FIG. 22 shows a perspective view of a multi-channel suture-tensioning device in accordance with one or more examples.

FIG. 22 shows a perspective view of a multi-channel suture-tensioning device 400 in accordance with one or more examples. In some contexts herein, the device 400 may be referred to as a cassette, and can include a plurality of bays 404 configured to have suture-tensioning devices in accordance with one or more examples of the present disclosure disposed therein.

With respect to the tensioning of multiple pairs of sutures during a procedure, as described herein, a single suture-tensioning device in accordance with certain aspects of the present disclosure may be utilized for the tensioning of a single suture, a pair of sutures, and/or multiple pairs of sutures together simultaneously in examples in which the relevant channels/conduits of the tensioning device are large enough to accommodate the desired number of sutures therein simultaneously. With multiple pairs of sutures drawn through a single suture-tensioning device at the same time, uniform tensioning may be achieved for all sutures and/or suture pairs therein. In implementations involving tensioning of plurality of sutures and/or suture pairs in a single suture-tensioning device, tension readings, such as may be achieved using one or more loadcells as described herein, may represent a some of the tension forces of all of the sutures. As an alternative, multiple pairs of sutures (or multiple sutures) may be tensioned separately using one or more suture-tensioning devices. For example, suture pairs may be tensioned one-by-one, either using separate tensioning devices, or a single suture-tensioning device that is moved from one pair of sutures (or one suture) to another pair of sutures (or another suture). The device 400 provides an example configuration of a suture-tensioning device cassette that allows for the individual tensioning of separate sutures or pairs of sutures in accordance with one or more examples of the present disclosure.

Certain advantages may be provided by tensioning pairs of sutures individually (e.g., one-by-one). For example, when utilizing imaging when tensioning sutures, adjustments of a single pair of sutures that is in a relatively higher or lower position than other pairs of sutures can be executed to adjust selectively among the pairs of sutures to achieve the desired balance and/or positioning. Furthermore, suture pairs can be iteratively tightened one-by-one to thereby provide improved precision in doing the procedure.

The assembly of FIG. 22 includes a tensioner cassette device 400, which may be configured to have disposed therein a plurality of separate suture-tensioning devices, which may be similar to the various examples of suture-tensioning devices disclosed in detail herein. Although the illustrated tensioner cassette 400 includes six slots/bays 404 for holding suture-tensioning devices or components, it should be understood that any suitable or desirable number of slots/bays may be included in a tensioner cassette device in accordance with the present disclosure.

In some examples, the bays 404 have a shape configured to receive correspondingly-shaped plunger track housing components. For example, in the illustrated example, the cassette bays 404 may have recesses configured to hold, in a rotationally secure manner, hexagonally-shaped suture-tensioning device components. With a plurality of suture-tensioning devices 401 secured in the tensioner cassette device 400, each of the plurality of tensioning devices 401 may be simultaneously, sequentially, and/or sporadically adjusted (e.g., manually by the operator) to adjust the respective sutures or suture pairs to achieve a desired tensioning results across the plurality of sutures or suture pairs. The respective tubes 405 of the suture-tensioning devices 401 are configured to apply the counter-acting load for each respective suture pair to the pledget 406, on which each of the tubes is resting and/or disposed.

Although the bays 404 of the cassette device 400 are shown as aligned in a row, it should be understood that the bays may be aligned in any suitable or desirable way. For example, the bays 404 may be vertically offset in series (e.g., with respect to the orientation shown in FIG. 22) to allow the devices 404 to be positioned relatively closer to one another. For example, alternating bays may open on opposite sides of the cassette device 400 to save space and/or provide a smaller form factor for the cassette device 400. In some examples, the cassette device 400 has a structure that allows for the bays to be arranged in a circular manner/arrangement.

Each of the plurality of bays 404 of the cassette structure 400 can be configured to receive and rotationally-secure a respective plunger track housing structure 401 of a suture-tensioning device, as shown. The suture-tensioning device(s) can have any of the features disclosed herein. In some examples, the plurality of bays are laterally arranged along at least a portion of a width dimension w of the cassette structure 400, as shown. In some examples, unlike the laterally-aligned arrangement shown in FIG. 22, adjacent bays of the plurality of bays 404 can be staggered. That is, laterally-adjacent bays (e.g., bays next to one another in the width dimension w) may be vertically-offset from one another with respect to the vertical dimension v of the illustrated orientation of the device 400. In some examples, a first subset of the plurality of bays are open on a topside of the cassette structure, whereas a second subset of the plurality of bays are open on a bottom side of the cassette structure. For reference, the bays 404 shown in FIG. 22 are illustrated as opening on the topside 409 of the structure 400, whereas the bottom side (not shown) is opposite the topside 409. Unlike the illustrate row arrangement of FIG. 22, in some examples, the bays are arranged in a circular arrangement, or another non-linear/row arrangement.

Figure 23:
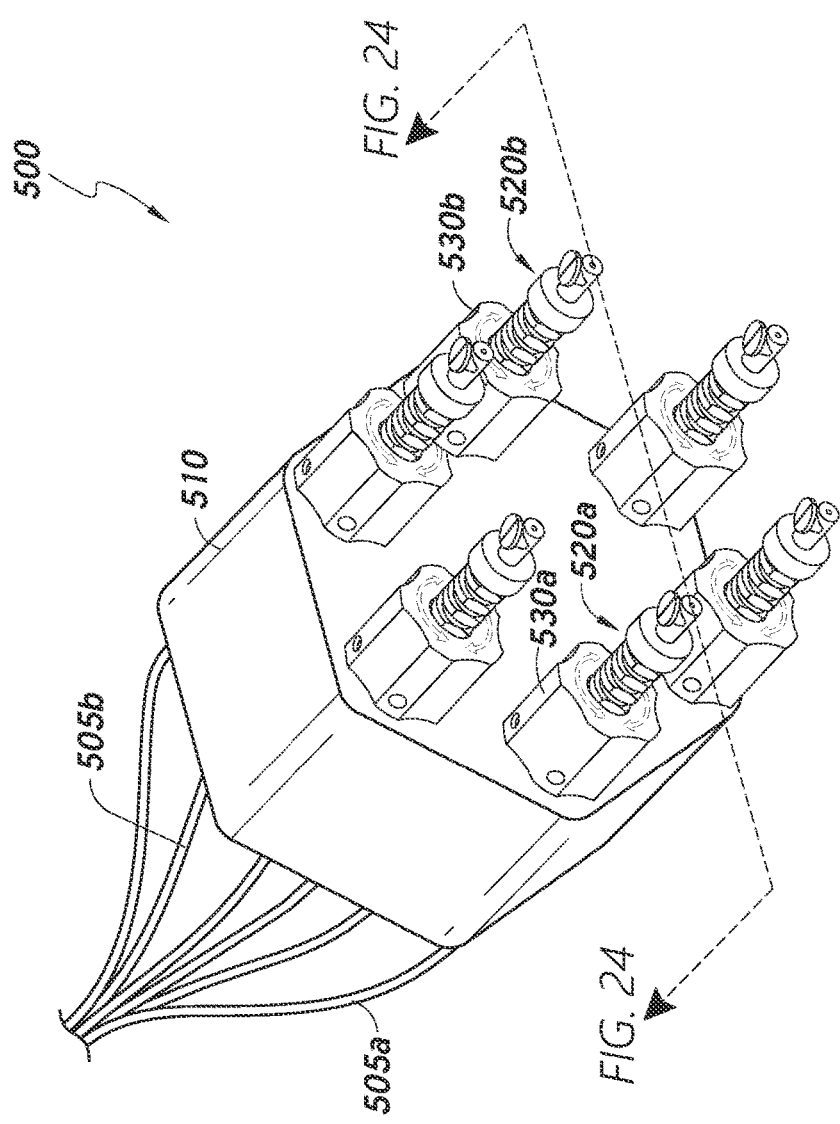
FIG. 23 shows a perspective view of a multi-channel suture-tensioning device in accordance with one or more examples.
Figure 24:
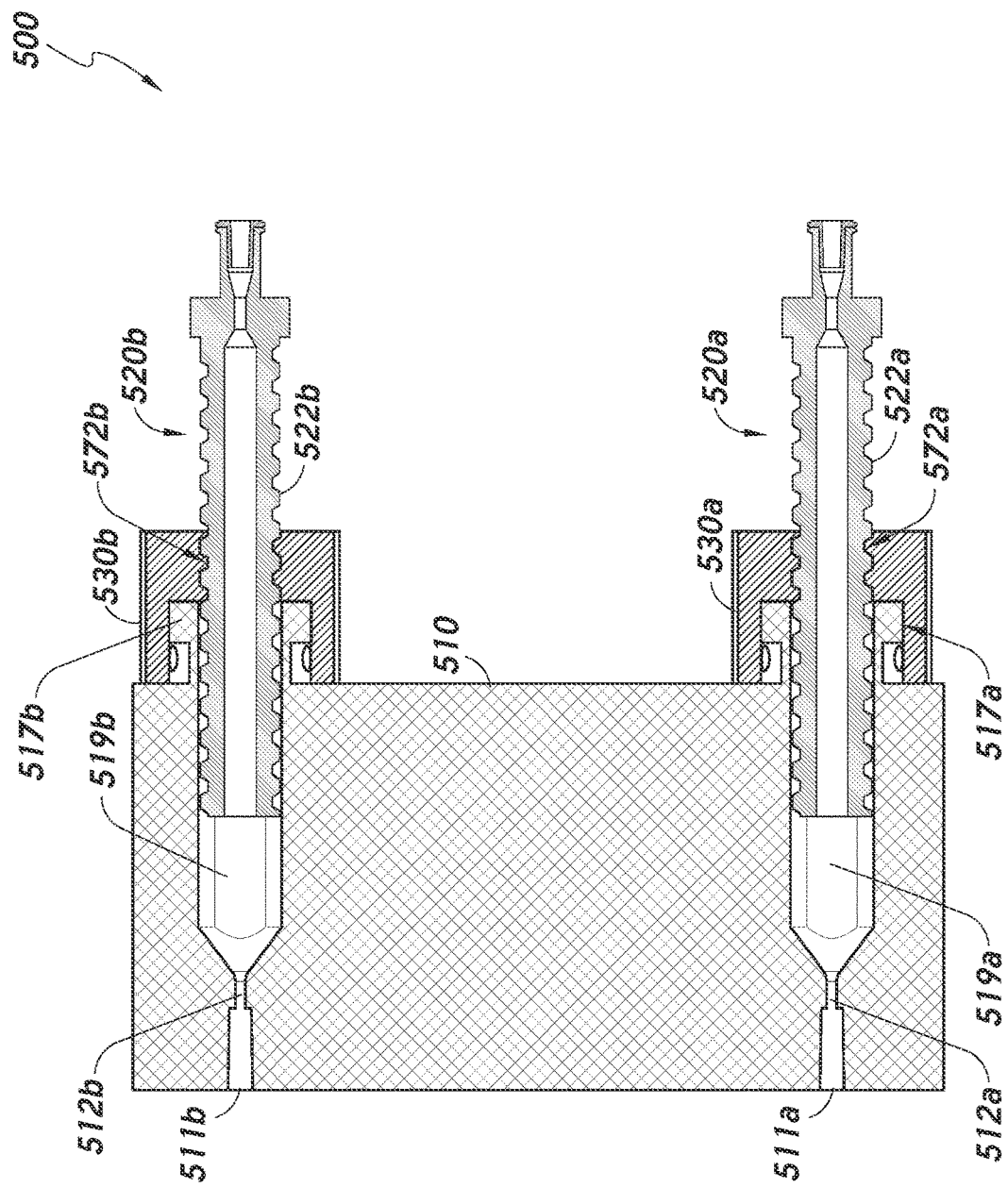
FIG. 24 is a side cross-sectional view of the multi-channel suture-tensioning device shown in FIG. 23 in accordance with one or more examples.

FIG. 23 shows a perspective view of a multi-channel suture-tensioning device 500 in accordance with one or more examples. FIG. 24 is a side cross-sectional view of the multi-channel suture-tensioning device shown in FIG. 23 in accordance with one or more examples.

The suture-tensioning device 500 includes a plunger channel housing structure 510 having formed therein a plurality of plunger tracks 519. In some examples, a suture-tensioning device may accommodate a plurality of separately-tensioned pairs of sutures, wherein a single device includes a plurality of plunger tracks 519, plungers 520, plunger actuators 530, and respective associated suture tubes 505. That is, unlike the cassette device 400 of FIG. 22, the device 500 of FIG. 23 may not include bays that receive independent/discrete suture-tensioning devices therein, but rather the device 500 may incorporate the necessary features of the individual suture-tensioning devices in a single device.

The tensioning device 500 may have any suitable or desirable form or shape, such as a bar, cylinder, hexagonal prism, or any other suitable or desirable shape or form. Furthermore, the device 500 and the various components thereof may have any of the characteristics of related features/devices disclosed above with respect to any of the other examples disclosed and/or illustrated in connection with the present disclosure, including but not limited to plunger screw threads, actuator threads, actuator axial retention features, tube-fit channels/recesses, suture-fixation features, and/or the like.

The plunger channel housing 510 includes a plurality of tube-access channels 511, which may be configured and/or dimensioned to be coupled with respective tubes 505. For example, the tubes 505 may fit within, and/or be received by, the channels 511, respectively, and may be secured thereto by a friction fit with the channels 511 and/or adhesive or other fixation means. In some examples, each of the tube-access channels 511 is open to a respective one of the plurality of plunger channels 519, such as via a connecting channel 512, which may be relatively narrow.

The plurality of elongate plungers 520 are each disposed at least partially within a respective one of the plurality of plunger channels 519 in an assembled configuration, as shown in FIGS. 23 and/or 24. The plurality of actuators 530 are rotatably coupled to the plunger channel housing structure 510. For example, the plunger channel housing structure 510 can include or be associated with a plurality of actuator-engagement structures 517 configured to be axially secured to the plurality of actuators 530, respectively.

In some examples, each of the actuators 530 can be configured to be actuated to cause axial displacement of a respective one of the plurality of plungers 520 with respect to the plunger channel housing structure 510.

Similarly to certain other examples of the present disclosure, the plurality of plungers 520 can each comprise one or more radially-outwardly projecting threads 522 that circumscribe an axial length/portion of the respective plunger. Furthermore, the plurality of actuators 530 can each comprise one or more radially-inwardly projecting threads 572 that are configured to engage with the threads 522 of a respective one of the plurality of plungers 520.

Figure 25:
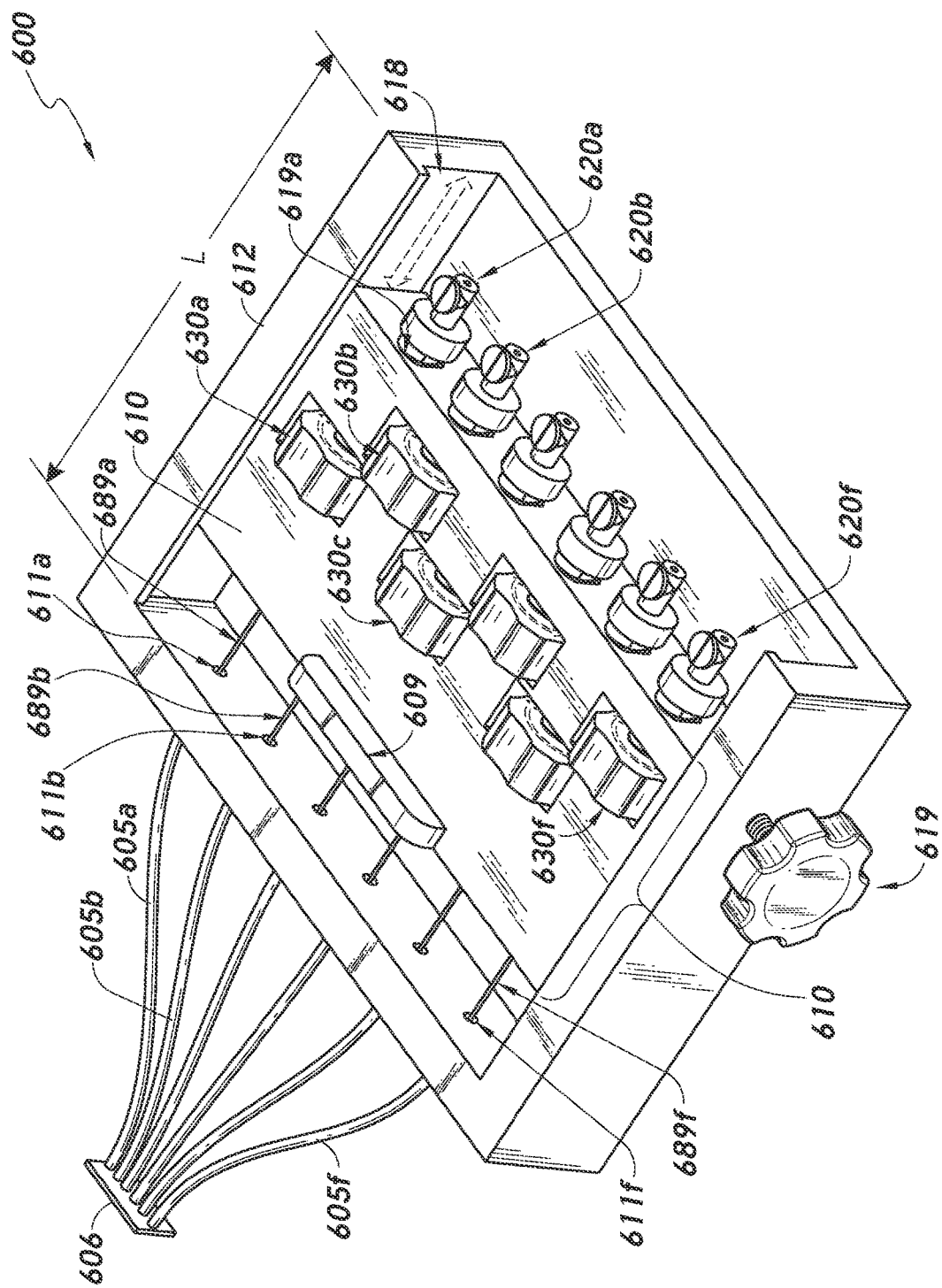
FIG. 25 is a perspective view of a multi-channel suture-tensioning device in accordance with one or more examples.

FIG. 25 shows a perspective view of a multi-channel suture-tensioning device 600 in accordance with one or more examples. The suture-tensioning device 600 includes a plunger channel housing structure 610 having formed therein a plurality of plunger tracks 619. The suture-tensioning device 600 may accommodate a plurality of separately-tensioned sutures or suture pairs 689, each of which is associated with a separate respective plunger track 619, plunger 620, plunger actuators 630, and suture tube 605.

The tensioning device 600 may have any suitable or desirable form or shape, such as a bar, rectangular prism, cylinder, hexagonal prism, or any other suitable or desirable shape or form. Furthermore, the device 600 and the various components thereof may have any of the characteristics of related features/devices disclosed above with respect to any of the other examples disclosed and/or illustrated in connection with the present disclosure, including but not limited to plunger screw threads, actuator threads, actuator axial retention features, tube-fit channels/recesses, suture-fixation features, and/or the like.

The plunger channel housing 610 includes a plurality of tube-access channels 611, which may be configured and/or dimensioned to be coupled with respective tubes 605. For example, the tubes 605 may fit within, and/or be received by, the channels 611, respectively, and may be secured thereto by a friction fit with the channels 611 and/or adhesive or other fixation means.

The plurality of elongate plungers 620 are each disposed at least partially within a respective one of the plurality of plunger channels 619 in an assembled configuration, as shown in FIG. 25. The plurality of actuators 630 are rotatably coupled to the plunger channel housing structure 610. For example, the plunger channel housing structure 610 can include or be associated with a plurality of actuator-engagement structures (not shown) configured to be axially secured to the plurality of actuators 630, respectively. In some examples, each of the actuators 630 can be configured to be actuated to cause axial displacement of a respective one of the plurality of plungers 620 with respect to the plunger channel housing structure 610.

Similarly to certain other examples of the present disclosure, the plurality of plungers 620 can each comprise one or more radially-outwardly projecting threads that circumscribe an axial length/portion of the respective plunger. Furthermore, the plurality of actuators 630 can each comprise one or more radially-inwardly projecting threads that are configured to engage with the threads 622 of a respective one of the plurality of plungers 620.

In some examples, the plunger channel housing structure is independently move in a dimension L to produce gross adjustment of the group of sutures/suture pairs 689 together. For example, the plunger channel housing can include a mechanical tab or other manually-manipulatable feature 609 that may be engaged by a user to cause relative movement of the housing 610 with respect to the frame structure 612. The housing 610 may be configured to slide within a track 618 associated with the frame 612. In some examples, the tube-access channels 611 are part of the frame 612. By sliding/moving the housing 610 relative to the frame 612, the sutures 689 can be adjusted as a group and/or by a common distance/amount. Gross movement/adjustment of the sutures 689 can be desirable to avoid putting too much tension on one suture, suture pair, and/or associated tissue anchor. By utilizing the gross movement functionality of the device 600, for example, it may be possible to draw a whole leaflet down together, rather than a single leaflet anchor.

The user may selectively adjust the individual actuators 630 and the gross movement tab/feature 609 to selectively adjust individual sutures or suture pairs versus a group of sutures or suture pairs. In some examples, the device 600 includes a locking mechanism 619 that may be used to lock the housing 610 in a fixed relative position within the track 618 with respect to the frame 612.

ADDITIONAL EXAMPLES

Depending on the example, certain acts, events, or functions of any of the processes or algorithms described herein can be performed in a different sequence, may be added, merged, or left out altogether. Thus, in certain examples, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain examples include, while other examples do not include, certain features, elements and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain examples require at least one of X, at least one of Y and at least one of Z to each be present.

It should be appreciated that in the above description of examples, various features are sometimes grouped together in a single example, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular example herein can be applied to or used with any other example(s). Further, no component, feature, step, or group of components, features, or steps are necessary or indispensable for each example. Thus, it is intended that the scope of the inventions herein disclosed and claimed below should not be limited by the particular examples described above but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which the examples belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

The spatially relative terms "outer," "inner," "upper," "lower," "below," "above," "vertical," "horizontal," and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A tensioning device comprising:
   an elongate plunger;
   a plunger track housing configured to receive the plunger therein at least in part, the plunger including first radially-projecting screw threading that is radially flattened over at least one circumferential segment of the plunger, the plunger track housing including an axial opening having a truncated circle shape and configured to fit the plunger therein;
   an elongate tube configured to be coupled to the plunger track housing; and
   an actuator configured to cause axial translation of at least a portion of the plunger within the plunger track housing, the actuator including second screw threading configured to made with the first screw threading of the plunger.

2. The tensioning device of claim 1, wherein the plunger has a suture-fixation feature associated therewith.

3. The tensioning device of claim 2, wherein the suture-fixation feature includes a Luer assembly.

4. The tensioning device of claim 2, wherein the suture-fixation feature includes a radially-projecting form configured to have suture wound thereabout.

5. The tensioning device of claim 1, wherein the plunger track housing includes a tube-fit channel open on a distal end of the plunger track housing and configured to receive a proximal end of the elongate tube.

6. The tensioning device of claim 1, wherein the actuator is configured to be rotatably secured to a proximal end of the plunger track housing.

7. The tensioning device of claim 6, wherein the plunger track housing includes a radially-open circumferential channel on a proximal side of the plunger track housing, the actuator comprising an engagement feature configured to be projected into the circumferential channel in a sliding engagement that allows for rotation of the actuator about the plunger track housing.

8. The tensioning device of claim 7, wherein:
   the engagement feature of the actuator comprises one or more setscrews configured to be disposed in one or more respective radially-oriented threaded apertures of the actuator; and
   the one or more apertures are configured to allow the one or more setscrews to project into the circumferential channel to axially secure the actuator to the plunger track housing.

9. The tensioning device of claim 1, further comprising a load cell device configured to generate signals indicative of an amount of tension force applied to a portion of the plunger.

10. The tensioning device of claim 9, wherein the load cell device is integrated with a proximal flange portion of the plunger.

11. The tensioning device of claim 10, wherein:
the plunger comprises a suture-attachment structure associated with a portion of the plunger that is on a proximal side of the proximal flange portion; and
the first radially-projecting screw threading is on a distal side of the proximal flange portion.

12. A method for tensioning sutures in a patient in need thereof, the method comprising:
drawing a suture through one or more channels of a suture-tensioning device;
fixing the suture to a plunger component of the suture-tensioning device, the plunger component including an elongate shaft with radially-oriented outer threading, the elongate shaft having a cross-sectional shape of a circle with at least one flat side; and
adjusting a relative axial position between the plunger component and a plunger track component of the suture-tensioning device by rotating an actuator about an axis of the plunger track component to thereby adjust a tension of a portion of the suture, the actuator including radially-oriented inner threading configured to engage with the outer threading of the elongate shaft of the plunger component;
wherein the plunger track component includes an axial inner channel dimensioned to receive at least a portion of the elongate shaft of the plunger component, the axial inner channel having at least one flat edge configured to contact the at least one flat side of the elongate shaft of the plunger component to restrain rotational movement of the plunger component relative to the plunger track component.

13. The method of claim 12, wherein said adjusting the relative axial position between the plunger component and the plunger track component involves manipulating an the actuator is slidingly coupled to the plunger component and the plunger track component.

14. The method of claim 13, wherein said rotating the actuator drives the outer threading of the elongate shaft of the plunger component using the inner threading of the actuator.

15. The method of claim 12, wherein said fixing the suture to the plunger component involves engaging the suture with a suture-fixation feature associated with a proximal portion of the plunger component.

16. The method of claim 12, further comprising:
snaring the suture with a snare wire disposed in, and axially traversing, the suture-tensioning device; and
drawing the suture proximally through an axial internal channel of the plunger component using the snare wire.

17. The method of claim 12, further comprising, after said adjusting the tension of the portion of the suture:
clamping the suture distal to the suture-tensioning device;
removing the suture-tensioning device from the suture; and
tying one or more knots with the suture while the suture is clamped to fix the tension of the portion of the suture.

18. The method of claim 12, wherein an axially-rigid tube extends distally from a distal end of the plunger track component, the suture passing through the axially-rigid tube.

* * * * *